(12) United States Patent
Kim

(10) Patent No.: US 10,241,060 B2
(45) Date of Patent: Mar. 26, 2019

(54) X-RAY IMAGING APPARATUS AND METHOD OF OPERATING SAME

(71) Applicant: Samsung Electronics Co., Ltd., Gyeonggi-do (KR)

(72) Inventor: Dae-soo Kim, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 240 days.

(21) Appl. No.: 15/156,615

(22) Filed: May 17, 2016

(65) Prior Publication Data

US 2016/0349191 A1 Dec. 1, 2016

(30) Foreign Application Priority Data

Jun. 1, 2015 (KR) .......................... 10-2015-0077487

(51) Int. Cl.
| | |
|---|---|
| *A61B 6/06* | (2006.01) |
| *G21K 1/04* | (2006.01) |
| *G01N 23/04* | (2018.01) |
| *G01N 23/00* | (2006.01) |
| *G21K 1/02* | (2006.01) |

(52) U.S. Cl.
CPC .............. *G01N 23/04* (2013.01); *A61B 6/06* (2013.01); *G21K 1/043* (2013.01); *G01N 2223/316* (2013.01); *G01N 2223/33* (2013.01)

(58) Field of Classification Search
CPC .. G01N 23/00; G01N 23/04; G01N 2223/316; G01N 2223/33; G21K 1/02; G21K 1/04; G21K 1/046; A61B 6/06
USPC ........................................ 378/147, 150, 152
See application file for complete search history.

(56) References Cited

U.S. PATENT DOCUMENTS

| | | | |
|---|---|---|---|
| 4,246,488 A | 1/1981 | Hura | |
| 7,440,550 B2 | 10/2008 | Xu | |
| 8,718,233 B2 | 5/2014 | Yuan | |

FOREIGN PATENT DOCUMENTS

| | | | |
|---|---|---|---|
| JP | 2014-83143 A | 5/2014 | |
| KR | 10-2012-0002357 A | 1/2012 | |

*Primary Examiner* — Jurie Yun
(74) *Attorney, Agent, or Firm* — Cha & Reiter, LLC.

(57) ABSTRACT

Provided is an X-ray imaging apparatus which includes a collimator configured to adjust an irradiation range of an X-ray irradiated from the X-ray source. The collimator comprises a first field size range adjustor comprising a first plurality of blades and a driving power transfer unit configured to transfer driving power to the first plurality of blades, a second field size range adjustor facing the first field size range adjustor and comprising a first plurality of blades, and a connector configured to respectively connect the first plurality of blades of the first field size range adjustor to the first plurality of blades of the second field size range adjustor so as to make the first plurality of blades of the second field size range adjustor move as the first plurality of blades of the first field size range adjustor move.

16 Claims, 16 Drawing Sheets

X-RAY IMAGING APPARATUS AND METHOD OF OPERATING SAME

CLAIM OF PRIORITY

This application claims the benefit of Korean Patent Application No. 10-2015-0077487, filed on Jun. 1, 2015, in the Korean Intellectual Property Office, the disclosure of which is incorporated herein in its entirety by reference for all purposes.

BACKGROUND

1. Field

One or more embodiments relate to an X-ray imaging apparatus and a method of operating the X-ray imaging apparatus.

2. Description of the Related Art

As the quality of medical care improves with rapid economic growth due to industrialization, there is increasing demand for apparatuses capable of capturing images of objects by using X-rays. Accordingly, there is increasing demand for X-ray imaging apparatuses.

X-ray imaging apparatuses for medical use are apparatuses use X-rays having excellent penetration capability to irradiate a targeted region of a human body and capture images of the inside of the body. An X-ray is a form of radiation. If the human body is exposed to radiation, it may damage body tissues and may cause a variety of diseases.

Including an X-ray radiation dose reduction device to minimize side effects on a patient due to radiation exposure in X-ray imaging, apparatuses can prevent such problems by minimizing side effects on a patient due to radiation exposure.

Including a collimator in X-ray imaging apparatuses for medical can appropriately adjust a range of X-ray radiation by regulating a range of X-rays moving vertically and horizontally. The collimator may typically include irises which may move vertically and horizontally to appropriately adjust a range of X-ray radiation.

For example, with some imaging methods, it may be beneficial to regulate the range of radiation of the collimator automatically or manually and to confirm the location of the collimator by using collimator light in order to limit the range of irradiation to a selected region of interest for precise imaging. However, this may be inconvenient and lead to an increased imaging time and inefficient operation motions on the part of users who operate the apparatuses.

SUMMARY

Provided are X-ray imaging apparatuses including a collimator configured to adjust an irradiation range of the X-ray irradiated from an X-ray source and methods of operating the X-ray imaging apparatuses.

According to an aspect of an embodiment, an X-ray imaging apparatus includes:

an X-ray source configured to irradiate an X-ray; and a collimator configured to adjust an irradiation range of the X-ray irradiated from the X-ray source, wherein the collimator comprises: a first field size range adjustor comprising a first plurality of blades and a driving power transfer unit configured to transfer driving power to the first plurality of blades; a second field size range adjustor facing the first field size range adjustor and comprising a first plurality of blades; and a connector configured to respectively connect the first plurality of blades of the first field size range adjustor to the first plurality of blades of the second field size range adjustor so as to make the first plurality of blades of the second field size range adjustor move as the plurality of first plurality of blades of the first field size range adjustor move. The driving power transfer unit may include a timing belt.

The timing belt may include a plurality of timing belts, wherein the plurality of timing belts includes a first timing belt and a second timing belt, the first plurality of blades of the first field size range adjustor includes a first blade and a second blade, a third blade and a fourth blade, wherein the first blade and the second blade of the first plurality of blades of the first field size range adjustor face each other and are fixed to the first timing belt; and the third and fourth blade of the first plurality of blades of the first field size range adjustor face each other and are fixed to the second timing belt.

The X-ray imaging apparatus may further include: a plurality of driving motors configured to transfer driving power to the timing belts including a first driving motor and a second driving motor, wherein the first driving motor is configured to transfer driving power to the first timing belt and the second driving motor is configured to transfer driving power to the second timing belt.

The X-ray imaging apparatus may further include: a controller configured to transfer a driving signal to the first driving motor and the second driving motor, wherein the controller transfers different control signals to the first driving motor and the second driving motor such that the first and second blade of the first plurality of blades of the first field range adjustor blades move independently from the third and fourth blade of the first plurality of blades of the first field range adjustor.

The X-ray imaging apparatus may further include: a first slide support unit configured to allow the first and second blade of the first plurality of blades of the first field range adjustor, the first slide support unit controlling a movement path of the first and second blade of the first plurality of blades of the first field range adjustor; and a second slide support unit configured to allow third and fourth blade of the first plurality of blades of the first field range adjustor to slide, the second slide support unit controlling the third and fourth blade of the first plurality of blades of the first field range adjustor.

The timing belt may include a plurality of timing belts, wherein the first and second blade of the first plurality of blades of the first field range adjustor which face each other and the third and fourth blade of the first plurality of blades of the first field range adjustor which face each other are respectively fixed to the plurality of timing belts.

The X-ray imaging apparatus may further include: a plurality of driving motors configured to transfer driving power to the timing belts; and wherein the plurality of driving motors are further configured to respectively transfer driving power to the plurality of timing belts.

The X-ray imaging apparatus may further include: a controller configured to transfer the driving signal to the plurality of driving motors, wherein the controller transfers different control signals to the plurality of driving motors such that the first, second, third, and fourth blades of the first plurality of blades of the first field range adjustor to move independently from each other.

The X-ray imaging apparatus may further include: a first slide support unit configured to allow the first and second blade of the first plurality of blades of the first field range adjustor to slide, the first slide support unit controlling a movement path of the first and second blade of the first plurality of blades of the first field range adjustor; and a second slide support unit configured to allow the third and fourth blade of the first plurality of blades of the first field range adjustor to slide, the second slide support unit controlling a movement path of the third and fourth blade of the first plurality of blades of the first field range adjustor.

The connector may include a connecting link arranged to revolve around a hinge unit, and a linking unit configured to respectively connect the first blades and the second blades by using the connecting link.

The linking unit may further include: a first long hole extending along a lengthwise direction of the connecting link in the surface of the connecting link; a first slider configured to be fixed to the first blade and to slide along a lengthwise direction of the first long hole; a second long hole extending along the lengthwise direction of the connecting link in the surface of the connecting link; and a second slider configured to be fixed to the second blade and to slide along a lengthwise direction of the second long hole.

A movement ratio of the first blade to the second blade which is connected to the first blade may be the same as a distance ratio of a distance from the hinge unit to the first slider to a distance from the hinge unit to the second slider.

According to another aspect of an embodiment, a method of operating the X-ray imaging apparatus described above includes: inputting an adjustment signal corresponding to a first field size range and an adjustment signal corresponding to a second field size range; moving the plurality of first blades; and moving the plurality of second blades in synchronization with the plurality of the first blades.

In the method, the plurality of the first blades may include a first, second, third, and fourth blade of the first plurality of blades of the first field range adjustor, and the first plurality fo blades of the second field range adjustor may include a first, second, third, and fourth blade, wherein the method may further include: generating a driving signal for a first driving motor and a second driving motor upon receiving the adjustment signal; generating driving power by the first driving motor and the second driving motor upon receiving the driving signal; and transferring the driving power generated by the first driving motor to the first and second blade of the first plurality of blades of the first field range adjustor and the driving power generated by the second driving motor to the third and fourth blade of the first plurality of blades of the first field range adjustor, respectively.

The method may further include providing independent driving signals to the first driving motor and the second driving motor; and moving the first and second blade of the first plurality of blades of the first field range adjustor independently from the third and fourth blade of the first plurality of blades of the first field range adjustor upon receiving the driving signal.

In the method, the first plurality of the blades of the first field range adjustor may include a 1st blade, a 2nd blade, a 3rd blade, and a 4th blade, and the first plurality of blades from the second field range adjustor may include a 1st blade, a 2nd blade, a 3rd blade, and a 4th blade; and wherein the method may further include: generating a driving signal for a plurality of driving motors upon receiving the adjustment signal; generating driving power at the plurality of driving motors upon receiving the driving signal; and transferring the driving power generated at the plurality of driving motors to each of the first, second, third, and fourth blades of the first plurality of blades of the first field range adjustor, respectively.

In the method, independent driving signals may be respectively provided to the plurality of driving motors; and the first, second, third, and fourth blades of the first plurality of blades of the first field range adjustor are moved independently from each other.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
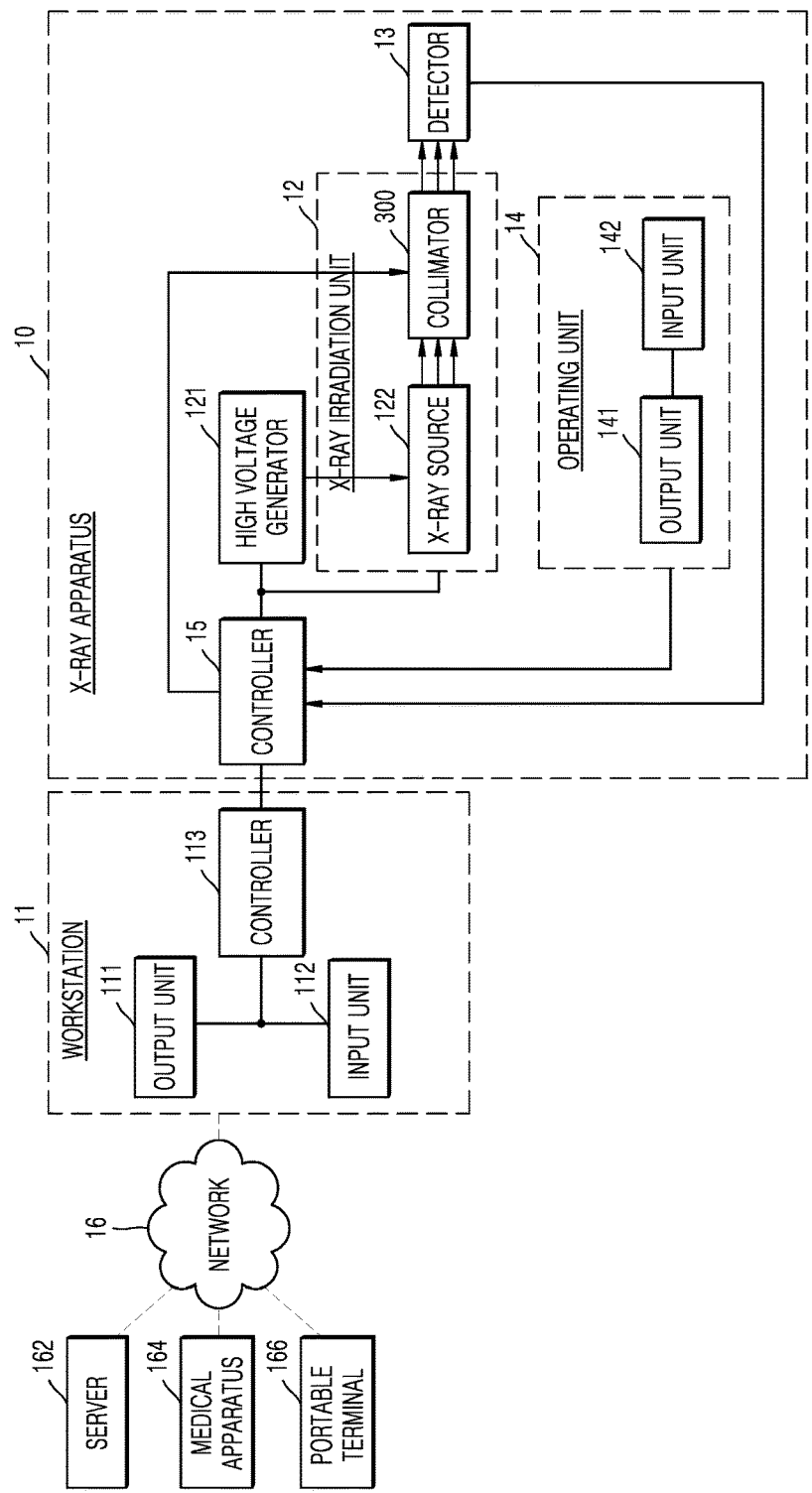
FIG. 1 is a view illustrating a structure of a X-ray imaging apparatus according to the an embodiment of the present disclosure.

The attached drawings for illustrating embodiments of the present disclosure are referred to in order to gain a sufficient understanding of the present disclosure, the merits thereof, and the objectives accomplished by the implementation of the present disclosure. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present invention will only be defined by the appended claims.

Hereinafter, the terms used in the specification will be briefly described, and then the present disclosure will be described in detail.

The terms used in this specification are those general terms currently widely used in the art in consideration of functions regarding the present disclosure, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, an "image" may denote multi-dimensional data composed of discrete image elements (for example, pixels in a two-dimensional image and voxels in a three-dimensional image). For example, an image may be a medical image of an object acquired by X-ray imaging apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

X-ray imaging apparatus is a medical imaging apparatus that acquires images of internal structures of an object by transmitting X-ray through the human body. The X-ray imaging apparatus may acquire medical images of an object more simply within a shorter time than other medical imaging apparatuses including an MRI apparatus and a CT apparatus. Therefore, the X-ray imaging apparatus is widely used in simple chest imaging, simple abdomen imaging, simple skeleton imaging, simple nasal sinuses imaging, simple neck soft tissue imaging, and breast imaging.

FIG. 1 is a view illustrating a structure of a X-ray imaging apparatus according to the related art. The X-ray imaging apparatus 10 shown in FIG. 1 may be a fixed-type X-ray imaging apparatus or a mobile X-ray imaging apparatus.

Referring to FIG. 1, the X-ray imaging apparatus 10 includes a workstation 11, an X-ray irradiation unit 12, a high voltage generator 121, and an X-ray detector 13.

The workstation 11 includes an input unit 112 through which a user may input commands for manipulating the X-ray imaging apparatus 10 including X-ray irradiation, and a controller 113 controlling overall operations of the X-ray imaging apparatus 10.

The high voltage generator 121 generates a high voltage for generating X-rays, and applies the high voltage to X-ray source 122.

The X-ray irradiation unit 12 includes the X-ray source 122 receiving the high voltage applied from the high voltage generator 121 to generate and irradiate the X-ray, and a collimator 300 for guiding a path of the X-ray irradiated from the X-ray source 122. The collimator 300 can include a first field size range adjustor having a plurality of blades and a driving power transfer unit to transfer driving power to the plurality of blades, a second field range adjustor facing the first field size range adjustor having a plurality of blades, and a connector connecting the plurality of blades of the first field size range adjustor and the second field size range adjustor, so that the second plurality of blades moves with the first plurality of blades. The collimator 300 will be described in greater detail in FIGS. 4-13.

The X-ray detector 13 detects X-ray that is radiated from the X-ray irradiation unit 12 and has been transmitted through an object.

Also, the X-ray imaging apparatus 10 may further include an operating unit 14 including a sound output unit 141 outputting sound representing information relating to imaging operation such as the X-ray irradiation under a control of the controller 113.

The workstation 11, the X-ray irradiation unit 12, the high voltage generator 121, and the X-ray detector 13 may be connected to each other via wires or wirelessly. If they are connected to each other wirelessly, a device (not shown) for synchronizing clocks with each other may be further included.

The input unit 112 may include a keyboard, a mouse, a touch screen, a voice recognizer, a fingerprint recognizer, an iris recognizer, and the like well known in the art. The user may input a command for irradiating the X-ray via the input unit 112, and to do this, the input unit 112 may include a switch for inputting the command. The switch may be configured so that an irradiation command for irradiating the X-ray may be input only when the switch is pushed twice.

That is, when the user pushes the switch, a prepare command for performing a pre-heating operation for X-ray irradiation may be input through the switch, and then, when the user pushes the switch once more, the irradiation command for irradiating the X-ray may be substantially input through the switch. When the user manipulates the switch as described above, the input unit 112 generates signals corresponding to the commands input through the switch manipulation, that is, a prepare signal and an irradiation signal, and outputs the generated signals to the high voltage generator 121 generating a high voltage for generating the X-ray.

When the high voltage generator 121 receives the prepare signal output from the input unit 112, the high voltage generator 121 starts a pre-heating operation, and when the pre-heating is finished, the high voltage generator 121 outputs a ready signal to the controller 121. In addition, the X-ray detector 13 also needs to prepare for detecting the X-ray, and thus, when the high voltage generator 121 receives the prepare signal output from the input unit 112, the high voltage generator 121 outputs a prepare signal to the X-ray detector 13 at the same time of performing the pre-heating operation, so that the X-ray detector 13 may prepare for detecting the X-ray transmitted through the object. The X-ray detector 13 prepares for detecting the X-ray when receiving the prepare signal, and when the preparing for the detection is finished, the X-ray detector 130 outputs a ready signal to the high voltage generator 121 and the controller 113.

When the pre-heating operation of the high voltage generator 121 is finished, the X-ray detector 13 is ready for the detecting the X-ray, and the irradiation signal is output from the input unit 112 to the high voltage generator 121, the high voltage generator 121 generates and applies the high voltage to the X-ray source 122, and the X-ray source 122 irradiates the X-ray.

When the irradiation signal is output from the input unit 112, the controller 113 may output a sound output signal to the sound output unit 141 so that the sound output unit 141 outputs predetermined sound and the object may recognize the irradiation of X-ray. Also, the sound output unit 141 may output sound representing other information relating to the imaging, in addition to the X-ray irradiation. In FIG. 1, the sound output unit 141 is included in the operating unit 14; however, the embodiments of the present disclosure are not limited thereto, and the sound output unit 141 may be located at a different location from the operating unit 14. For example, the sound output unit 141 may be included in the workstation 11, or may be located on a wall surface of an examination room in which the X-ray imaging of the object is performed.

The controller 113 controls locations of the X-ray irradiation unit 12 and the X-ray detector 13, an imaging timing, and imaging conditions according to imaging conditions set by the user.

In more detail, the controller 113 controls the high voltage generator 121 and the X-ray detector 13 according to the command input via the input unit 112 so as to control an irradiation timing of the X-ray, an intensity of the X-ray, and an irradiation region of the X-ray. Also, the controller 113 adjusts the location of the X-ray detector 13 according to a predetermined imaging condition, and controls an operation timing of the X-ray detector 13.

In addition, the controller 113 generates a medical image of the object by using image data transmitted from the X-ray detector 13. In detail, the controllers 112 may receive the image data from the X-ray detector 13, and then, generate the medical image of the object by removing noise from the image data and adjusting a dynamic range and interleaving of the image data.

The X-ray imaging apparatus 10 shown in FIG. 1 may further include an output unit (not shown) for outputting the medical image generated by the controller 113. The output unit may output information that is necessary for the user to manipulate the X-ray imaging apparatus 10, for example, a user interface (UI), user information, or object information. The output unit may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a three-dimensional (3D) display, a transparent display, and other various output devices well known in the art.

The workstation 11 shown in FIG. 1 may further include a communicator (not shown) that may be connected to a server 162, a medical apparatus 164, and a portable terminal 166 via a network 16.

The communication unit may be connected to the network 16 via wires or wirelessly to communicate with the external server 162, the external medical apparatus 164, or the external portable terminal 166. The communicator may transmit or receive data related to diagnosis of the object via the network 16, and may also transmit or receive medical images captured by the medical apparatus 164, for example, a CT apparatus, an MRI apparatus, or X-ray imaging apparatus. Moreover, the communicator may receive a medical history or treatment schedule of an object (e.g., a patient) from the server 162 to diagnose a disease of the object. Also, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module is a module for communicating by using an electric signal or an optical signal, and the wired communication technology may be wired communication technology using a pair cable, a coaxial cable, or an optical fiber cable, and a wired communication technology that is well known in the art.

The wireless communication module may transmit/receive a wireless signal to/from at least one of a base, an external device, and a server in a mobile communication network. Here, the wireless signal may be a voice call signal, a video call signal, or various types of data according to text/multimedia messages transmission.

The X-ray imaging apparatus 10 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, the communication between the workstation 11 and the X-ray irradiation unit 12, the workstation 11 and the high voltage generator 121, and the workstation 11 and the X-ray detector 13 may use a high speed digital interface, such as low voltage differential signalling (LVDS), asynchronous serial communication, such as universal asynchronous receiver transmitter (UART), synchronous serial communication, or a low latency network protocol, such as a controller area network (CAN), and other various communication methods that are well known in the art may be used.)

Figure 2:
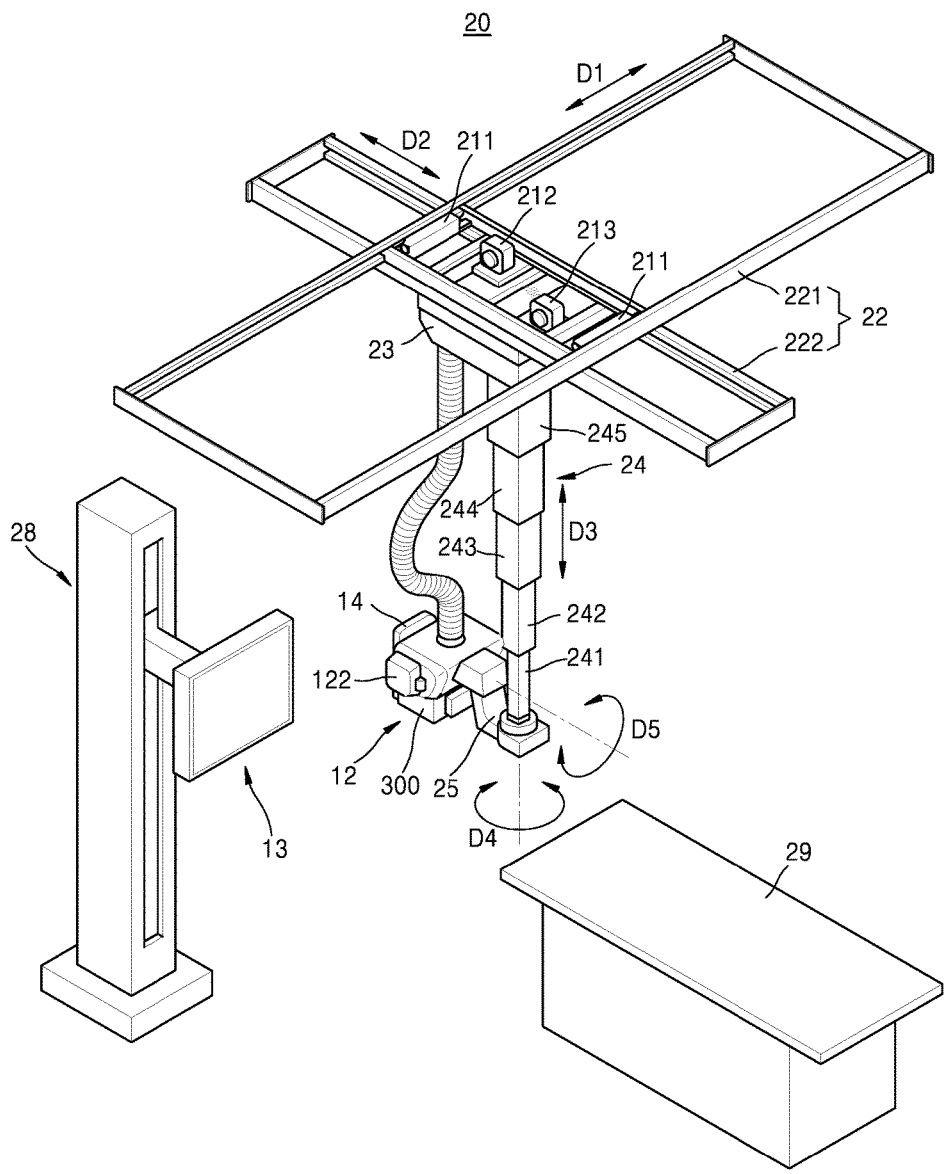
FIG. 2 is a perspective view illustrating a fixed-type X-ray imaging apparatus, according to an embodiment of the present disclosure.

FIG. 2 is a perspective view illustrating a fixed-type X-ray imaging apparatus, according to an embodiment.

Referring to FIG. 2, the fixed type X-ray imaging apparatus 20 includes an operating unit 14 providing a user with an interface for manipulating the X-ray imaging apparatus 20, X-ray irradiation unit 12 radiating X-ray to an object, a X-ray detector 13 detecting X-ray that has passed through the object, motors 211, 212, and 213 providing a driving power to transport the X-ray irradiation unit 12, a guide rail 22, a moving carriage 23, and a post frame 24. The guide rail 22, the moving carriage 23, and the post frame 24 are formed to transport the X-ray irradiation unit 12 by using the driving power of the motors 211, 212, and 213.

The guide rail 22 includes a first guide rail 221 and a second guide rail 222 that are provided to form a predetermined angle with respect to each other. The first guide rail 221 and the second guide rail 222 may be substantially perpendicular to each other, respectively extend in directions crossing each other at substantially 90°.

The first guide rail 221 can be provided on the ceiling of an examination room in which the X-ray imaging apparatus 20 is disposed.

The second guide rail 222 can be located under the first guide rail 221, and mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 23 is disposed under the second guide rail 222 so as to move along the second guide rail 222. A roller (not shown) moving along the second guide rail 222 may be provided on the moving carriage 23.

Therefore, the moving carriage 23 may move in the first direction D1 together with the second guide rail 222, and may move in the second direction D2 along the second guide rail 222.

The post frame 24 is fixed on the moving carriage 23 and located under the moving carriage 23. The post frame 24 may include a plurality of posts 241, 242, 243, 244, and 245.

The plurality of posts 241, 242, 243, 244, and 245 are telescopically connected to each other, and thus, the post frame 24 may have a length that is adjustable in a vertical direction of the examination room while in a state of being fixed to the moving carriage 23.

A third direction D3 is defined as a direction in which the length of the post frame 24 increases or decreases. Therefore, the third direction D3 may be perpendicular to the first direction D1 and the second direction D2.

The X-ray irradiation unit 12 may include the X-ray source 122 and the collimator 300 which regulates the radiation range of X-rays generated and irradiated by the X-ray source 122. The X-ray source 122 includes an X-ray tube that may be realized as a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The high voltage generator 121 may be included in the X-ray source 122, but is not limited thereto, and may be included somewhere else in the X-ray imaging apparatus 20.

The X-ray detector 13 detects X-rays that have passed through the object, and may be configured either as a table-type 29 X-ray detector 13 or as a stand-type 28 X-ray detector 13. The X-ray detector 13 may be implemented by using a thin film transistor (TFT) or a charge coupled device (CCD).

A rotating joint 25 is disposed between the X-ray irradiation unit 12 and the post frame 24. The rotating joint 25 allows the X-ray irradiation unit 12 to be coupled to the post frame 24, and supports a load applied to the X-ray irradiation unit 12.

The X-ray irradiation unit 12 connected to the rotating joint 25 may rotate on a plane that is perpendicular to the third direction D3. In this case, a rotating direction of the X-ray irradiation unit 12 may be defined as a fourth direction D4.

Also, the X-ray irradiation unit 12 may be configured to be rotatable on a plane perpendicular to the ceiling of the examination room. Therefore, the X-ray irradiation unit 12 may rotate in a fifth direction D5 that is a rotating direction about an axis that is parallel with the first direction D1 or the second direction D2, with respect to the rotating joint 25.

The motors 211, 212, and 213 may be provided to move the X-ray irradiation unit 12 in the first, second, and third directions D1, D2, and D3. The motors 211, 212, and 213 may be electrically driven, and the motors 211, 212, and 213 may respectively include an encoder.

The motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 23. In another example, the motors 211, 212, and 213 may be connected to a driving power transfer unit (not shown) so as to linearly move the X-ray irradiation unit 12 in the first, second, and third directions D1, D2, and D3. The driving power transfer unit may be a combination of a belt and a pulley, a combination of a chain and a sprocket, or a shaft, which are generally used.

In another example, motors (not shown) may be disposed between the rotating joint 25 and the post frame 24 and between the rotating joint 25 and the X-ray irradiation unit 12 in order to rotate the X-ray irradiation unit 12 in the fourth and fifth directions D4 and D5.

On one side of the X-ray irradiation unit 12, an operating unit 14 is included which provides an interface that allows entering of various input information and controlling of each device.

Although FIG. 2 shows the fixed type X-ray imaging apparatus 20 connected to the ceiling of the examination room, the fixed type X-ray imaging apparatus 20 is merely an example for convenience of comprehension. That is, X-ray imaging apparatuses according to embodiments of the present disclosure may include X-ray imaging apparatuses having various other structures such as, for example, a C-arm-type X-ray imaging apparatus and an angiography X-ray imaging apparatus, in addition to the fixed type X-ray imaging apparatus 20 of FIG. 2.

Figure 3:
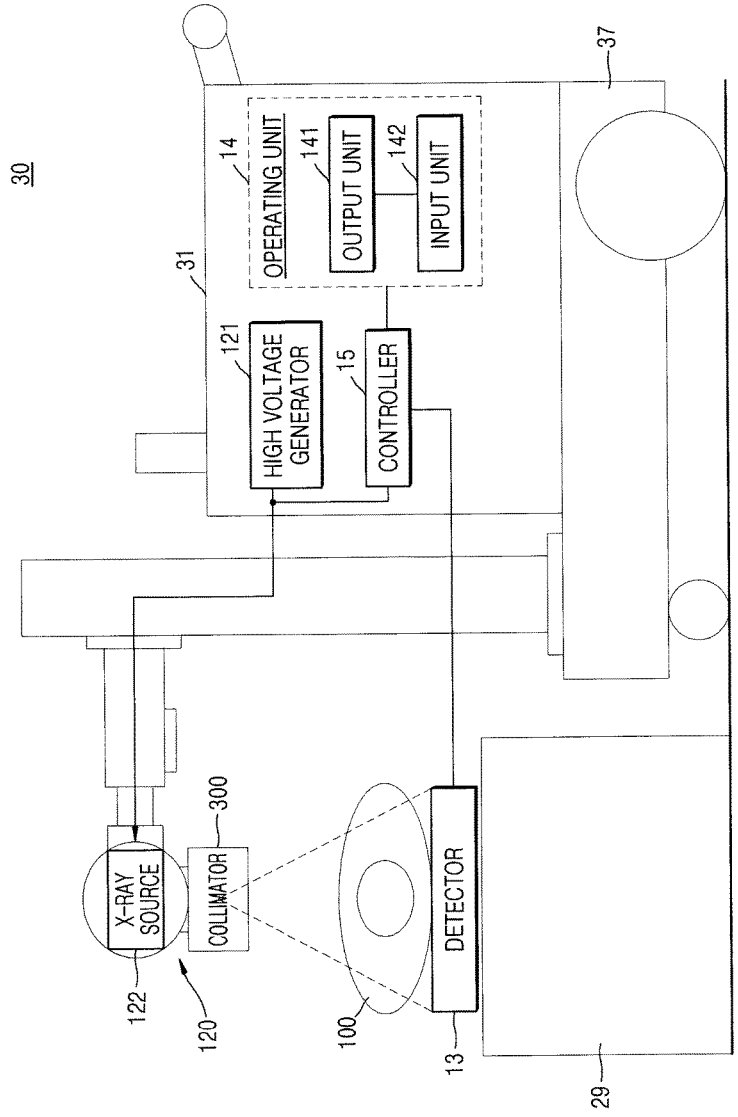
FIG. 3 is a view illustrating a mobile X-ray imaging apparatus capable of capturing X-ray images without being affected by an imaging location, according to an embodiment of the present disclosure.

FIG. 3 is a view illustrating the mobile X-ray imaging apparatus capable of capturing X-ray images without being affected by an imaging location, according to an embodiment.

An X-ray apparatus 30 shown in FIG. 3 may include a moving unit 37 including a wheel for facilitating the movement of the X-ray apparatus 30; a main unit including an input unit 142 receiving commands for operating the X-ray apparatus 30, a high voltage generator 121 generating high voltage applied to the X-ray source 122, a sound output unit 141 outputting sounds indicating imaging-related information such as X-ray irradiation, and a controller 15 controlling overall operation of the X-ray apparatus 30; the X-ray irradiation unit 12 including the X-ray source 122 generating X-rays and the collimator 300 for guiding a path of the X-rays irradiated from the X-ray source 122; and the X-ray detector 13 which detects X-rays that are radiated from the X-ray irradiation unit 12 and have penetrated an object.

The input unit 142 receives some input from the user. The input unit 142 may include a keyboard, a mouse, a touch screen, a voice recognizer, a fingerprint recognizer, an iris recognizer, and the like well known in the art. The user may input a command for irradiating the X-ray via the input unit 142, and to do this, the input unit 142 may include a switch for inputting the command. The switch may be configured so that an irradiation command for irradiating the X-ray may be input only when the switch is pushed twice.

That is, when the user pushes the switch, a prepare command for performing a pre-heating operation for X-ray irradiation may be input through the switch, and then, when the user pushes the switch once more, the irradiation command for irradiating the X-ray may be substantially input through the switch. When the user manipulates the switch as described above, the input unit 142 generates signals corresponding to the commands input through the switch manipulation, that is, a prepare signal and an irradiation signal, and outputs the generated signals to the high voltage generator 121 generating a high voltage for generating the X-ray.

When the high voltage generator 121 receives the prepare signal output from the input unit 142, the high voltage generator 121 starts a pre-heating operation, and when the pre-heating is finished, the high voltage generator 121 outputs a ready signal to the controller 15. In addition, the X-ray detector 13 also needs to prepare for detecting the X-ray, and thus, when the high voltage generator 121 receives the prepare signal output from the input unit 142, the high voltage generator 121 outputs a prepare signal to the X-ray detector 13 at the same time of performing the pre-heating operation, so that the X-ray detector 13 may prepare for detecting the X-ray transmitted through the object. The X-ray detector 13 prepares for detecting the X-ray when receiving the prepare signal, and when the preparing for the detection is finished, the X-ray detector 130 outputs a ready signal to the high voltage generator 121 and the controller 15.

When the pre-heating operation of the high voltage generator 121 is finished, the X-ray detector 13 is ready for the detecting the X-ray, and the irradiation signal is output from the input unit 142 to the high voltage generator 121, the high voltage generator 121 generates and applies the high voltage to the X-ray source 122, and the X-ray source 122 irradiates the X-ray. When the irradiation signal is output from the input unit 142, the controller 15 may output a sound output signal to the sound output unit 141 so that the sound output unit 141 outputs predetermined sound and the object may recognize the irradiation of X-ray. Also, the sound output unit 141 may output sound representing other information relating to the imaging, in addition to the X-ray irradiation.

In FIG. 3, the sound output unit 141 is included in the main unit 31; however, embodiments are not limited thereto. For example, the sound output unit 141 may be located where the mobile X-ray apparatus 30 is located (e.g., on a wall of a hospital room(.

The controller 15 controls locations of the X-ray irradiation unit 12 and the X-ray detector 13, an imaging timing, and imaging conditions according to imaging conditions set by the user.

In addition, the controller 15 generates a medical image of the object by using image data transmitted from the X-ray detector 13. In detail, the controllers 113 and 15 may receive the image data from the X-ray detector 13, and then, generate the medical image of the object by removing noise from the image data and adjusting a dynamic range and interleaving of the image data.

The main unit 31 of the X-ray apparatus 30 shown in FIG. 3 may further include an output unit (not shown) which outputs a medical image generated by the controller 15. The output unit may output information that is necessary for the user to manipulate the X-ray imaging apparatus 30, for example, a user interface (UI), user information, or object information.

Figure 4:
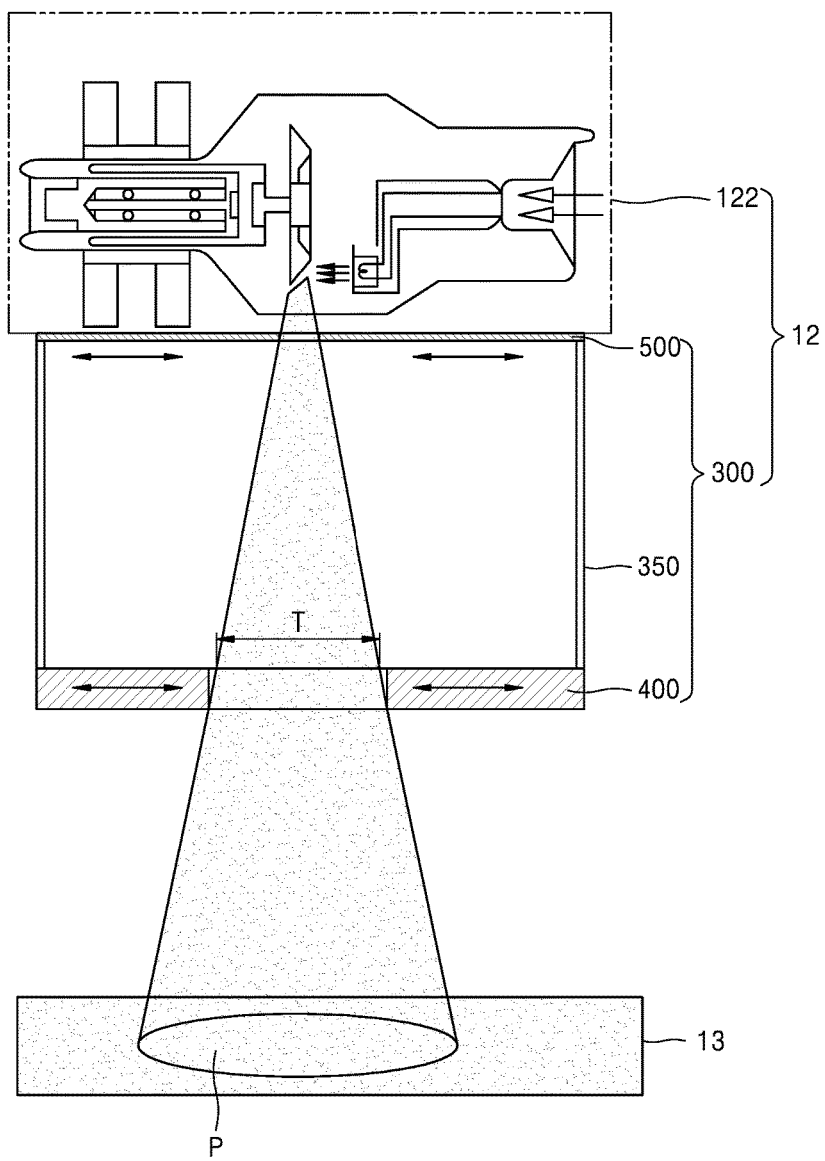
FIG. 4 is schematic view of an X-ray irradiator, according to an embodiment of the present disclosure.
Figure 5:
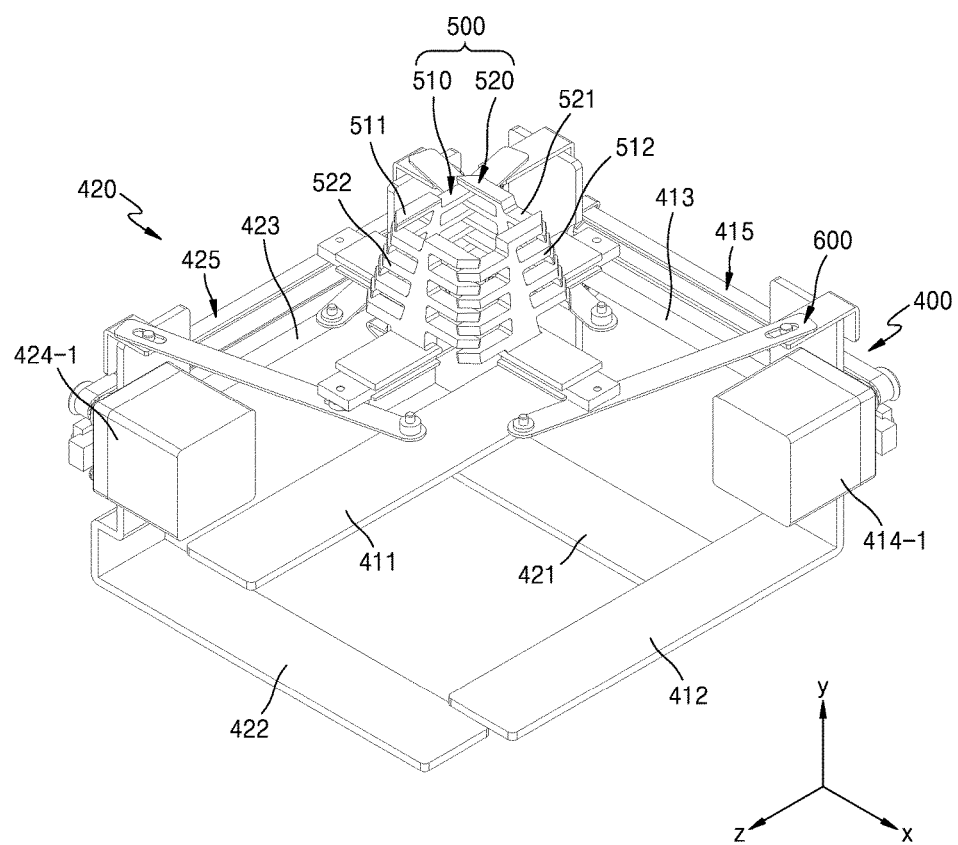
FIG. 5 is a perspective view illustrating a collimator, according to an embodiment of the present disclosure.
Figure 6A:
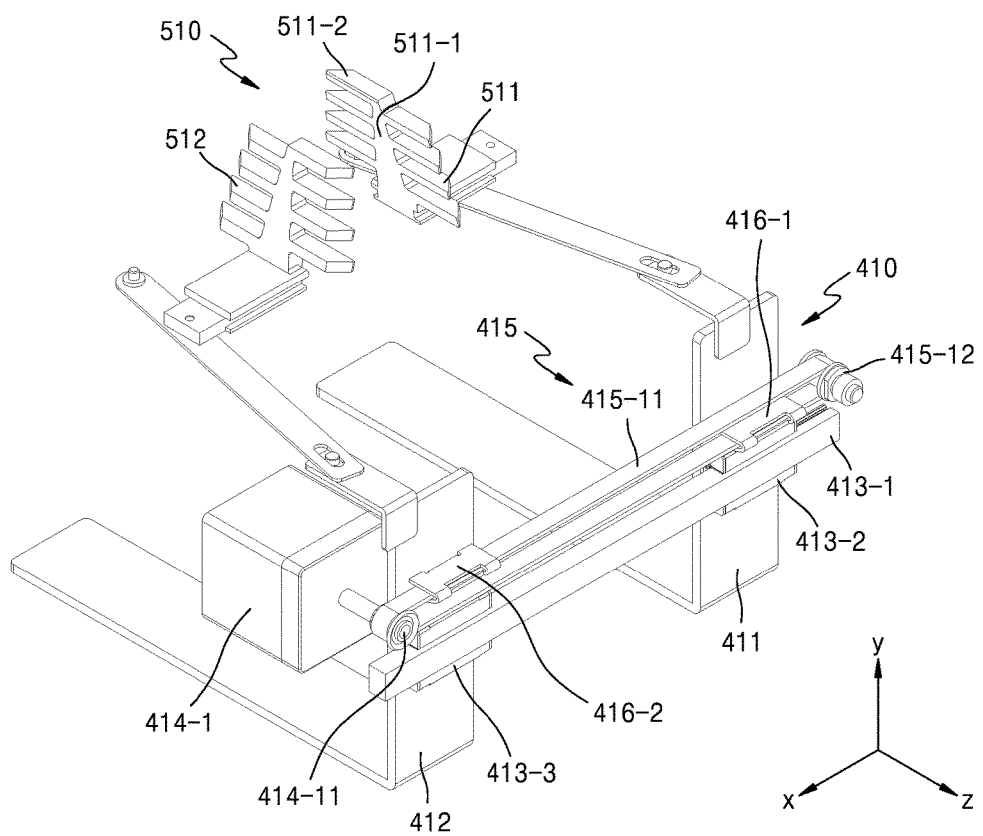
FIG. 6A is a partially-cut perspective view illustrating a first iris unit and a first blocking unit included in the collimator as shown in FIG. 5, according to an embodiment of the present disclosure.
Figure 6B:
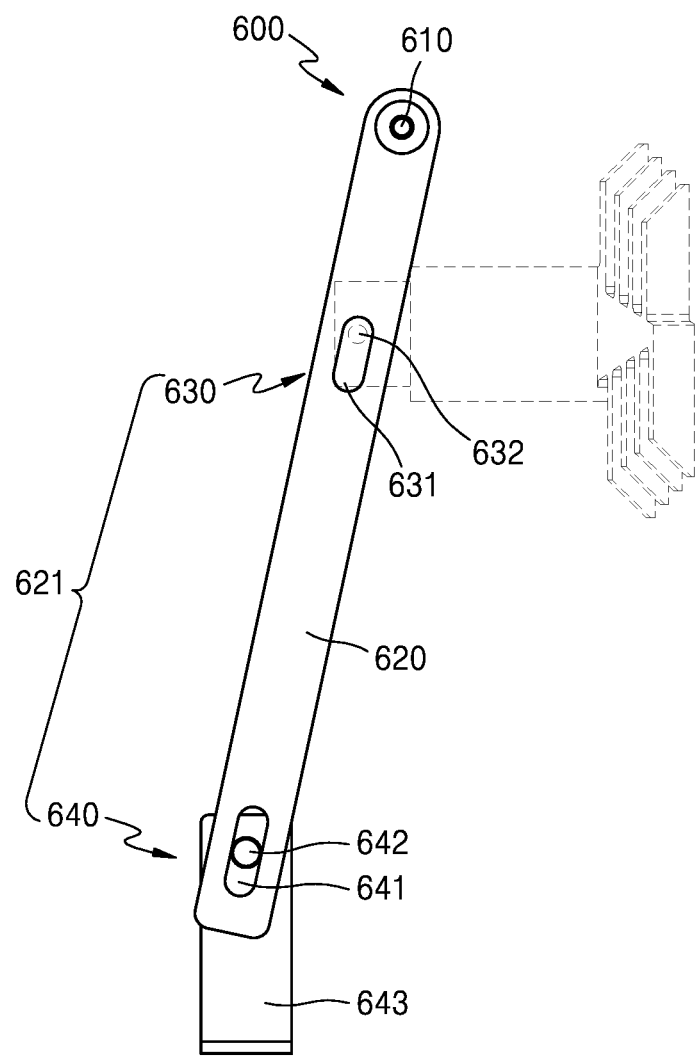
FIG. 6B is a partial plan view illustrating the first iris unit and the first blocking unit included in the collimator as shown in FIG. 5, according to an embodiment of the present disclosure.

FIG. 4 is schematic view of X-ray irradiation unit 12, according to an embodiment. FIG. 5 is a perspective view illustrating a collimator, according to an embodiment. FIG. 6A is a partially-cut perspective view illustrating a first iris unit and a first blocking unit included in the collimator as shown in FIG. 5, according to an embodiment. FIG. 6B is a partial plan view illustrating the first iris unit and the first blocking unit included in the collimator as shown in FIG. 5, according to an embodiment.

Referring to FIGS. 4 through 6B, the collimator 300 may include a housing 350 which forms a certain space, a first field size range adjustor for controlling the first field size range P, a second field size range adjustor 500 which is arranged to face the first field size range adjustor 400 so as to control the second field size range T, and a connector 600 arranged between the first field size range adjustor 400 and the second field size range adjustor 500.

The first field size range adjustor 400 is an iris unit which is arranged at a bottom end of the housing 350 and may include a first iris unit 410 which adjusts the field size range along the X-axis and a second iris unit 420 which adjusts the field size range along the Z-axis.

The a rear view of the first iris unit 410 is shown separated from the remainder of the collimeter 300 in FIG. 6A. The first iris unit 410 may include a blade 411 moving along the X-axis, a blade 412, a first slide support unit 413 which supports the 1st blade 411 and the blade 412, a first driving motor 414-1 which generates driving power to move the blade 411 and the blade 412, a first driving power transfer unit 415 which may transfer the driving power generated by the first driving motor 414-1 to the blade 411 and the blade 412.

In various embodiments, the blade 411 and the blade 412 may be formed in the form of capital letter "L" and may be arranged to be spaced apart and parallel from each other with a gap therebetween. The blade 411 and the blade 412 may be movable along the X-axis and an X-ray may pass through a void formed between the blade 411 and the blade 412.

In some embodiments, the blade 411 and the blade 412 may include a material such as lead, bismuth, silver, or tungsten having a property of absorbing X-rays irradiated by the X-ray source 122. Accordingly, it is possible to reduce an external leakage of X-rays which are not able to pass through the collimator 300. However, the present embodiment is not limited thereto, and it is possible to reduce an external leakage of X-rays which are not able to pass through the collimator 300, by providing a special coating film, which includes a material having a property of absorbing X-rays, on one side of the blade 411 and the blade 412.

The first slide support unit 413 is a support member to control the blade 411 and the blade 412, and may be arranged so as to slide with the blade 411 and the blade 412. According to one embodiment, the first slide support unit 413 may include a slide support bar 413-1 extending along the X-axis and the first slide member and the second slide member 413-2 and 413-3 that may slide along the slide support bar 413-1 in the direction of the X-axis.

The first slide member and the second slide member 413-2 and 413-3 may be connected to slide over the slide support bar 413-1, and may be arranged while being fixed to the blade 411 and the blade 412. Thus, the first slide member and the second slide member 413-2 and 413-3 may move the blade 411 and the blade 412 along the direction of extension of the slide support bar 413-1 (i.e., in the direction of the X-axis(.

The first driving motor 414-1 is a driving member capable of generating driving power to move the blade 411 and the blade 412, and an output axis 414-11 of the first driving motor 414-1 may be connected to the first driving power transfer unit 415.

The first first driving power transfer unit 415 is a driving power transfer member that may transfer the driving power generated at the first driving motor 414-1 to the blade 411 and the blade 412. In various embodiments, the first driving power transfer unit 415 may include a timing belt 415-11 which is supported to revolve around an output axis 414-11 and move according to a rotation of the output axis 414-11 and a support axis 415-12 which is arranged to face the output axis 414-11 and may support the timing belt 415-11.

The timing belt 415-11 may be arranged to revolve around the output axis 414-11 and the support axis 415-12 while being supported by the output axis 414-11 and the support axis 415-12. In this case, the first connecting member 416-1 and the second connecting member 416-2 may be arranged to be fixed to the timing belt 415-11 which moves in different directions along the X-axis. As a result, a first connecting member 416-1 and a second connecting member 416-2 may be moved in different directions along the path of the timing belt 415-11, and the blade 411 and the blade 412, which are arranged to be fixed to the first connecting member 416-1 and the second connecting member 416-2, also may be moved in different directions along the path of the timing belt 415-11.

A second iris unit 420 may include a blade 421 moving along the Z-axis, a blade 422, a second slide support unit 423 supporting the blade 421 and the blade 422, a second driving motor 424-1 generating driving power to move the blade 421 and the blade 422, a second driving power transfer unit 425 to transfer driving power generated from the second driving motor 424-1 to the blade 421 and the blade 422.

The blade 421 and the blade 422 may be formed in the form of capital letter "L" and may be arranged to be spaced apart with a gap. The blade 421 and the blade 422 may be moveable along the Z-axis and X-rays may pass through a void formed between the blade 421 and the blade 422.

The blade 421 and the blade 422 may be arranged on the upper portion of the blade 411 and the blade 412. As a result, X-rays radiating from the X-ray source 122 may be irradiated toward an object by passing through an overlapped area of a void formed between the blade 411 and the blade 412 and a void formed between the blade 421 and the blade 422.

As related information about a second slide support unit 423, a second driving motor 424-1 and a second driving power transfer unit 425 included in a second iris unit 420 is virtually the same as that about the first slide support unit 413, the first driving motor 414-1 and the first driving power transfer unit 415 included in the first iris unit 410, redundant descriptions will be omitted herein.

The second field size range adjustor 500 is an iris unit which is arranged at a top end of the housing 350 and may include a first blocking unit 510 which adjusts the field size range along the X-axis and a second blocking unit 520 which adjusts the field size range along the Z-axis.

The first blocking unit 510 may include the 1st blade 511 and the 2nd blade 512 moveable along the X-axis, and the second blocking unit 520 may include the blade 521 and the blade 522 moving along the Z-axis.

The blades 511, 512, 521 and 522 may be plate-like members inclined at angles to an optical axis, and may include a material such as lead, bismuth, silver, or tungsten having a property of absorbing X-rays irradiated by the X-ray source 122. In various embodiments, as shown in FIG. 6, the blade 511 may be formed as a fish bone-type blade, and may include a core unit 511-1 which extends at an angle from the optical axis and a plurality of frame units 511-2 which extend perpendicularly to the direction in which the core unit 511-1 extends. As a result, in the case that the blades 511, 512, 521 and 522 are arranged to be close to one another, the plurality of frame units 511-2 included in the blades 511, 512, 521 and 522 may be arranged to interleave with one another. As a result, the blades 511, 512, 521 and 522 may be moved close to one another without interfering with one another.

X-rays may pass through a void formed between the blade 511 and the blade 512 along the X-axis, and may pass through a void formed between the blade 521 and the blade 522 along the Z-axis. Accordingly, in the case that the blade 511 and the blade 512 move closer to each other along the X-axis, a void through which the X-rays pass along the X-axis may become narrow, and in the case that the blade 511 and the blade 512 move farther away from each other along the X-axis, a void through which the X-rays pass along the X-axis may become wide. In some embodiments, in the case that the blade 521 and the blade 522 move closer to each other along the Z-axis, a void through which the X-rays pass along the Z-axis may become narrow, and in the case that the blade 521 and the blade 522 move farther from each other along the Z-axis, a void through which the X-rays pass along the Z-axis may become wide.

As previously described in detail, as the blades 511, 512, 521 and 522 may be moved close to one another without interfering with one another, X-rays radiating from the X-ray source 122 may be irradiated toward an object by passing through an overlapped area of a void formed between the blade 511 and the blade 512 and a void formed between the blade 521 and the blade 522.

A connector 600 is a connecting member which connects the blades 411, 412, 421 and 422 to the blades 511, 512, 521 and 522, respectively. In various embodiments, the connector 600 may include a linking unit 621 with a connecting unit 620 that may revolve around a hinge unit 610.

The linking unit 621 has a linking structure to connect the first blade 410 and the second blade 420 by using the connecting unit 620. As previously described in detail, the connecting unit 620 may revolve around the hinge unit 610 while the first blade 410 and the second blade 420 connected to the connecting unit 620 may move linearly, according to an embodiment. As a result, the linking unit 621 may include the connecting unit 620, a first slide unit 630 which has a link joint slide along the lengthwise direction of the connecting unit 620, and a second slide unit 640.

The connecting unit 620 is a linear connecting member formed to be extended in one direction, and may be arranged to revolve around the hinge unit 610 which is provided at one end. In various embodiments, the connecting unit 620 may be revolved as the blades 411, 412, 421 and 422 move, and as the connecting unit 620 revolves, the blades 511, 512, 521 and 522 which are arranged to be fixed to a first slider 632, to be described in detail hereinafter, may move in the direction of the axis X or the axis Z.

The first slide unit 630 may include a first long hole 631 which extends along the direction of extension of the connecting unit 620 and a first slider 632 which slides while being inserted into the first long hole 631. The first long hole 631 is a slide guide member which is able to control a movement direction of the first slider 632, and may be arranged at either end of the connecting unit 620.

The first slider 632 is a slide member which may slide along the lengthwise direction of the first long hole 631, while being inserted into the first long hole 631. The first slider 632 may be arranged to be fixed to each of the blades 511, 512, 521 and 522, respectively, As a result, the blades 511, 512, 521 and 522 may move together as the first slider 632 slides.

The second slide unit 640 may include a second long hole 641 which extends along the direction of extension of the connecting unit 620 and a second slider 642 which slides while being inserted into the second long hole 641. The second long hole 641 is a slide guide member which is able to control a movement direction of the second slide unit 642, and may be arranged between the first long hole 631 and one end of the connecting unit 620 where the hinge unit 610 is not provided.

The second slider 642 is a slide member which may slide along the lengthwise direction of the second long hole 641, while being inserted into the second long hole 641. The second slider 642 may be arranged to be fixed to each of the blades 411, 412, 421 and 422, respectively. In this case, a joint 643 may be arranged between the second slide unit 642 and the blades 411, 412, 421 and 422. The joint 643 may be fixed to the second slide unit 642 and the blades 411, 412, 421 and 422. As a result, the second slide unit 642 may be fixed to the blades 411, 412, 421 and 422. However, the present embodiment is not limited thereto, and the second slide unit 642 may be arranged to be fixed directly to each of the blades 411, 412, 421 and 422, respectively. As a result, the second slide unit 642 may slide along the lengthwise direction of the second long hole 641 as the blades 411, 412, 421 and 422 move.

Figure 7:
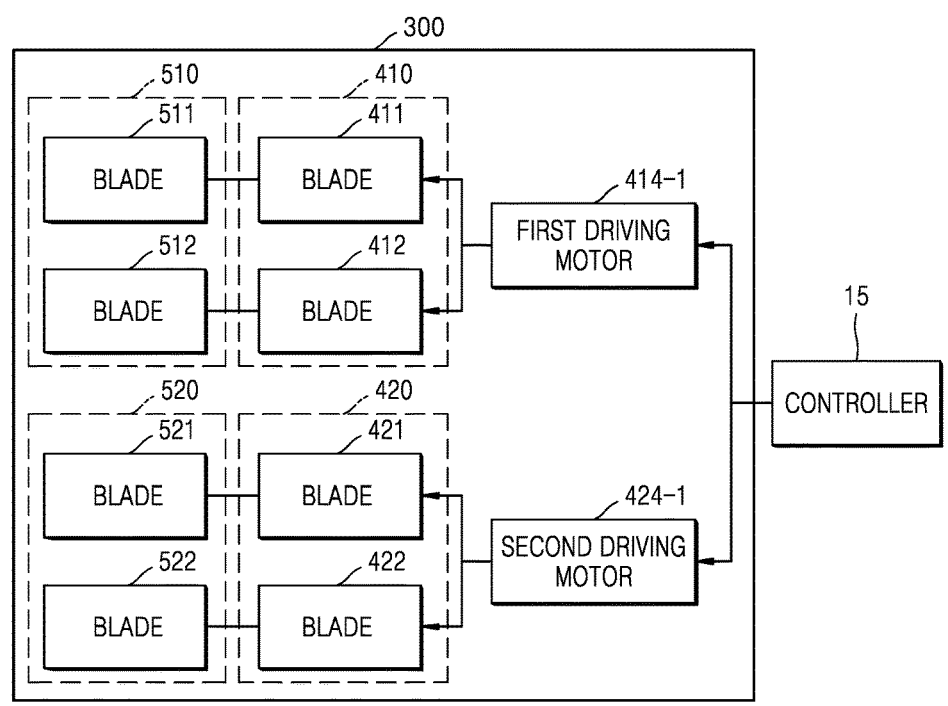
FIG. 7 is a block diagram illustrating a structure of the collimator, according to an embodiment of the present disclosure.
Figure 8:
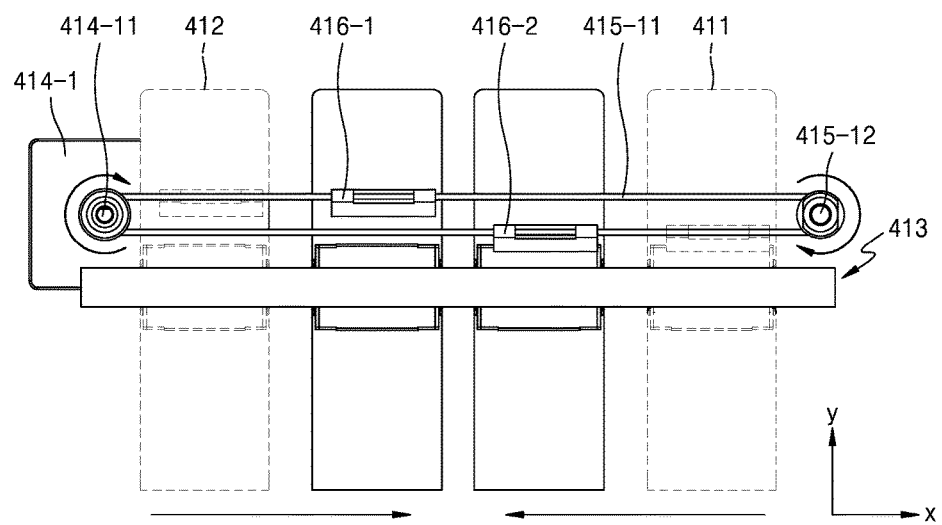
FIG. 8 is a partial front view illustrating the first iris unit which shows a movement status of first and second blades of the first field range adjustor, according to an embodiment of the present disclosure.
Figure 9:
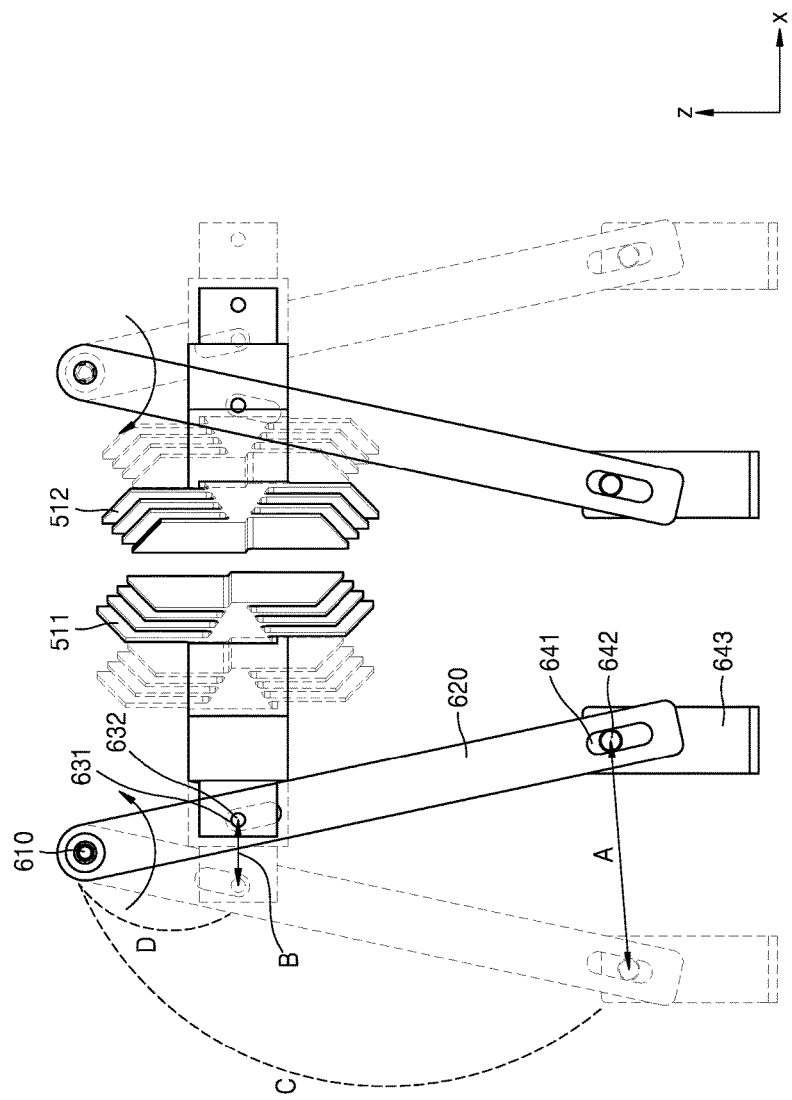
FIG. 9 is a partial plan view illustrating the first blocking unit which shows a movement status of the first and second blades of the first field range adjustor blades, according to an embodiment of the present disclosure.

FIG. 7 is a block diagram illustrating a structure of the collimator, according to an embodiment. FIG. 8 is a partial front view illustrating the first iris unit which shows a movement status of the blades 411, 412, according to an embodiment. FIG. 9 is a partial plan view illustrating the first blocking unit which shows a movement status of the 1st and 2nd blades 511 and 512, according to an embodiment.

Referring to FIG. 7, the blade 411 and the blade 412 included in the first iris unit 410 may be moved by receiving driving power generated by the first driving motor 414-1. In this process, the blade 511 and the blade 512 included in the first blocking unit 510 may be connected to the blade 411 and the blade 412 so as to move in synchronization, respectively.

In some embodiments, the blade 421 and the blade 422 included in the second iris unit 420 may be moved by receiving driving power generated by the second driving motor 424-1. In this process, the blade 521 and the blade 522 included in the second blocking unit 520 may be connected to the blade 421 and the blade 422 so as to move in synchronization, respectively. Hereinafter, for convenience of explanation, movements of the blade 411 and the blade 412 and the and blades 511 and 521 will be described by mainly focusing on the blade 411 and the blade 412 included in the first iris unit 410 and the blade 511 and the blade 521 included in the first blocking unit 510.

Referring to FIGS. 8 and 9, as driving power is generated by the first driving motor 414-1, an output axis 414-11 may rotate. The timing belt 415-11 which is supported by the output axis 414-11 and the support axis 415-12 so as to revolve may revolve in the same direction as the output axis 414-11 rotates. In various embodiments, in the case that the output axis 414-11 rotates clockwise, the timing belt 415-11 may also revolve clockwise.

As the timing belt 415-11 revolves clockwise, a first connecting member 416-1 and a second connecting member 416-2 arranged to be fixed to the timing belt 415-11 may move in different directions along the X-axis. In this case, as the first connecting member 416-1 and the second connecting member 416-2 are arranged to be fixed to one timing belt 415-11, the two may move in synchronization. Accordingly, as the timing belt 415-11 revolves, the first connecting member 416-1 and the second connecting member 416-2 may move in different directions but a same distance.

The blade 411 and the blade 412 fixed to each of the first connecting member 416-1 and the second connecting member 416-2 may move in different directions along the X-axis together with the first connecting member 416-1 and the second connecting member 416-2. As the blade 411 and the blade 412 move in different directions along the X-axis, a separation distance may be adjusted between the blade 411 and the blade 412, and the first field size range P made by the blade 411 and the blade 412 along the X-axis may also be adjusted.

As the adjustment of the first field size range P along the Z-axis caused by the movement of the second driving motor 424-1 and the blade 421 and the blade 422 is virtually the same as the adjustment of the first field size range P along the X-axis caused by the movement of the blade 411 and the blade 412, explanations thereof will be omitted herein.

As previously described in detail, as the blade 411 and the blade 412 move along the X-axis, the second slide unit 642 connected to be fixed to each of the blade 411 and the blade 412 may also move along the X-axis, by using the joint 643. In this process, the second slide unit 642 may slide along the direction of extension of the second long hole 641. In some embodiments, as the second slide unit 642 slides along the direction of extension of the second long hole 641, the connecting unit 620 may revolve around the hinge unit 610. As the connecting unit 620 revolves around the hinge unit 610, the first slider 632 inserted in the first long hole 631 may also slide along the direction of extension of the first long hole 631. As a result, the blade 511 and the blade 512 arranged to be fixed to the first slider 632 may slide along the X-axis, and it may result in an adjustment of the second field size range T.

In various embodiments, as the blade 411 moves toward the blade 412 along the X-axis, the second slide unit 642 arranged to be fixed to the blade 411 may also move toward the blade 412 along the X-axis. In this case, the second slide unit 642 may slide to move closer to the hinge unit 610 along the direction of extension of the second long hole 641. As a result, the connecting unit 620 may revolve around the hinge unit 610 counter-clockwise. As the connecting unit 620 revolves around the hinge unit 610 counter-clockwise, the first slider 632 inserted in the first long hole 631 may slide to become closer to the hinge unit 610 along the direction of extension of the first long hole 631. As a result, the blade 511 arranged to be fixed to the first slider 632 may move to become close to the blade 512 along the X-axis, and as a result it may adjust the second field size range T.

As the movement of the blade 521 and the blade 522 connected to the blade 421 and the blade 422 so as to work in synchronization with each other is virtually the same as that of the blades 421 and 422, explanations thereof will be omitted herein.

As the movement of the blades 411, 412, 421 and 422 works in synchronization with the blades 511, 512, 521 and 522, the first field size range P and the second field size range T may be adjusted in proportion to each other. In various embodiments, as the blade 411 moves a first moving distance A along the X-axis, the second slide unit 642 arranged to be fixed to the blade 411 moves the first moving distance A along the X-axis. In this case, the first slider 632 arranged to work in synchronization with the second slide unit 642 due to the connecting unit 620 may move a second moving distance B along the X-axis. As a result, the blade 511 arranged to be fixed to the first slider 632 may also move the second moving distance B along the X-axis.

In addition, in the path of moving of the connecting unit 620, the first slider 632 and the second slide unit 642 caused by the movement of the blade 411 and the blade 511, the first moving distance A and the second moving distance B of the first slider 632 and the second slide unit 642 may be proportionate to a first separation distance C and a second separation distance D from the hinge unit 610 to the first and the second sliders 632 and 642. For example, a ratio of the first separation distance C from the hinge unit 610 to the second slide unit 642 to the second separation distance D from the hinge unit 610 to the first slider 632 may be the same as the first moving distance A of the second slide unit 642 moving along the X-axis and the second moving distance B of the first slide unit 632 moving along the X-axis. Accordingly, in the case that the ratio of the first separation distance C and the second separation distance D from the hinge unit 610 to the first slider 632 and the second slider 642 is adjusted, a ratio of the first field size range P to the second field size range T which may be formed by the blade 411 and the blade 511 arranged to work in synchronization with each other may be adjusted.

When moving the blade 411 and the blade 412 and the blade 511 and the blade 512 connected to the blade 411 and the blade 412 by using the timing belt 415-11 connected to the first driving motor 414-1, a symmetric adjustment alone is possible for the first field size range P and the second field size range T because the blade 411 and the blade 412 may move in synchronization with each other. By contrast, in the case that the driving motor or the timing belt to drive the blade 411 and the blade 412 is provided, it is easier to adjust the first field size range P and the second field size range T, because the blade 411 and the blade 412 may move more independently.

Figure 10:
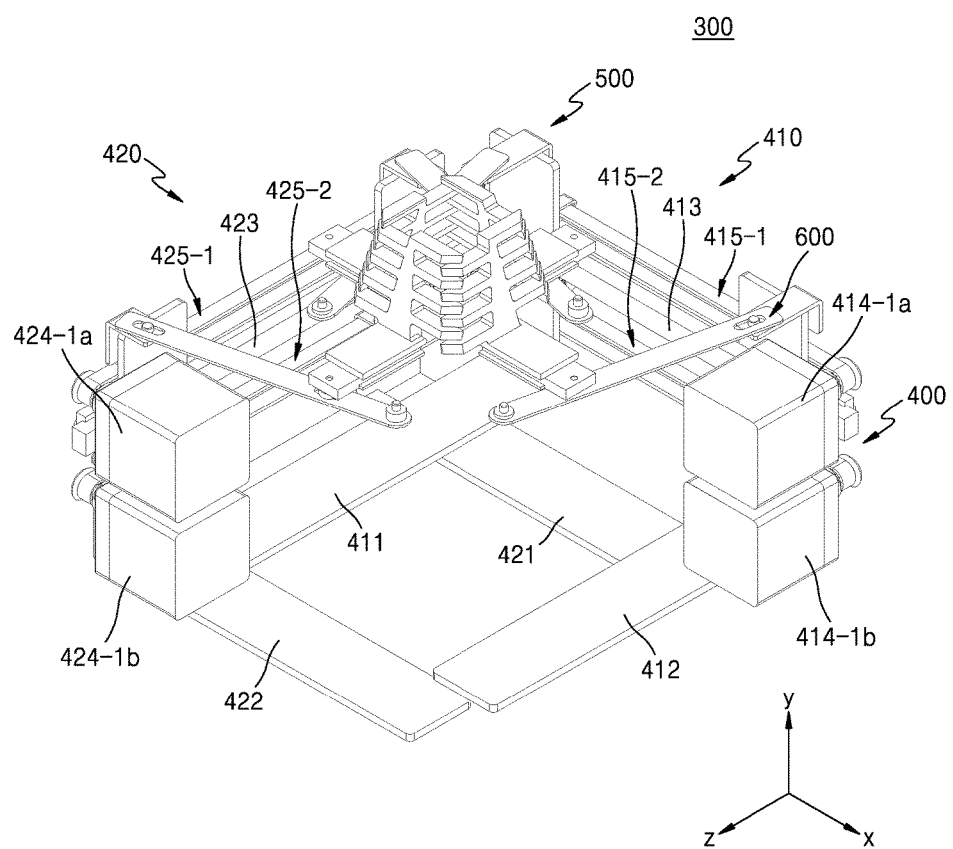
FIG. 10 is a perspective view illustrating the collimator, according to another embodiment of the present disclosure.
Figure 11:
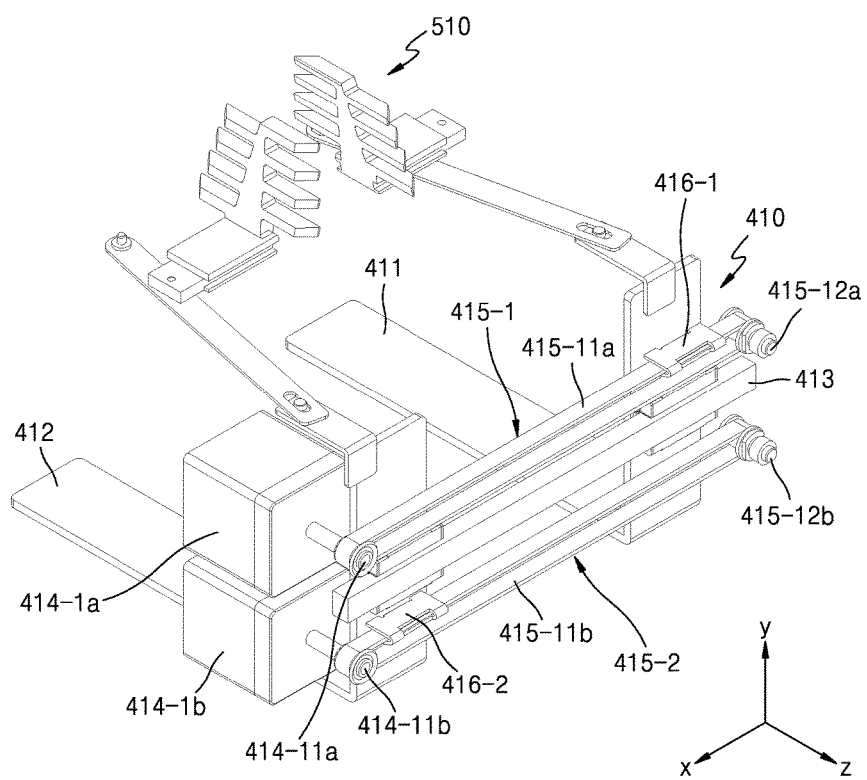
FIG. 11 is a perspective view illustrating a first iris unit and a first blocking unit included in the collimator as shown in FIG. 10, according to an embodiment of the present disclosure.

FIG. 10 is a perspective view illustrating the collimator, according to another embodiment. FIG. 11 is a perspective view illustrating the first iris unit and the first blocking unit included in the collimator as shown in FIG. 10, according to an embodiment. For the convenience of explanation, descriptions of virtually the same structures as those described in FIGS. 5 and 6 will be omitted herein.

Referring to FIGS. 10 and 11, a first iris unit 410 according to another embodiment may include a blade 411 that may move along the X-axis, a blade 412, a first slide support unit 413 that may support the blade 411 and the blade 412, a driving motor 414-1*a* generating driving power for moving each of the blade 411 and the blade 412, a driving motor 414-1*b*, and the 1st driving power transfer unit 415-1 and the driving power transfer unit 415-2 that may transfer driving power generated by the driving motor 414-1*a* and the driving motor 414-1*b* to the blade 411 and the blade 412.

The driving motor 414-1*a* and the driving motor 414-1*b* are driving members that may move the blade 411 and the blade 412. The driving power transfer unit 415-1 may be connected to a first output axis 414-11*a* of the driving motor 414-1*a* while the driving power transfer unit 415-2 may be connected to a second output axis 414-11*b* of the driving motor 414-1*b*.

The driving power transfer unit 415-1 and the driving power transfer unit 415-2 are driving power transferring members that may transfer driving power generated by the driving motor 414-1*a* and the driving motor 414-1*b* to the blade 411 and the blade 412, respectively. In various embodiments, the driving power transfer unit 415-1 may include the first timing belt 415-11*a* which may move due to a revolution of the first output axis 414-11*a* while being arranged to face the first output axis 414-11*a* and the first support axis 415-12*a* that may support the first timing belt 415-11*a* while being arranged to face the first output axis 414-11*a*. In some embodiments, the driving power transfer unit 415-2 may include the second timing belt 415-11*b* which may move due to a rotation of the second output axis 414-11*b* while being arranged to face the second output axis 414-11*b* and the second support axis 415-12*b* that may support the second timing belt 415-11*b* while being arranged to face the second output axis 414-11*b*.

The first timing belt 415-11*a* may be arranged to revolve around the first output axis 414-11*a* and the first support axis 415-12*a* while being supported by the first output axis 414-11*a* and the first support axis 415-12*a*. In some embodiments, the second timing belt 415-11*b* may be arranged to revolve around the second output axis 414-11*b* and the second support axis 415-12*b* while being supported by the second output axis 414-11*b* and the second support axis 415-12b. In this case, the first connecting member 416-1 and the second connecting member 416-2 may be arranged to be fixed to the first timing belt 415-11a and the second timing belt 415-11b, respectively. As a result, the first connecting member 416-1 and the second connecting member 416-2 may be moved individually along the path of the first timing belt 415-11a and the second timing belt 415-11b. The blade 411 and the blade 412 which are arranged to be fixed to the first connecting member 416-1 and the second connecting member 416-2 may also be moved along the path of the first timing belt 415-11a and the second timing belt 415-11b.

The second iris unit 420 may include the blade 421 that may move along the Z-axis, the blade 422, the second slide support unit 423 that may support the blade 421 and the blade 422, a driving motor 424-1a generating driving power for moving each of the blade 421 and the blade 422, a driving motor 424-1b, and the 2-1st driving power transfer unit 425-1 and the driving power transfer unit 425-2 that may transfer driving power generated by the 2-1st driving motor 424-1a and the driving motor 424-1b to the blade 421 and the blade 422.

As the 2-1st driving motor 424-1a, the driving motor 424-1b, the 2-1st driving power transfer unit 425-1 and the driving power transfer unit 425-2 which are included in the second iris unit 420 may be virtually the same as the 1-1st driving motor 414-1a, the driving motor 414-1b, the 1-1st driving power transfer unit 415-1 and the driving power transfer unit 415-2 of the first iris unit 410, explanations thereof will be omitted herein.

Figure 12:
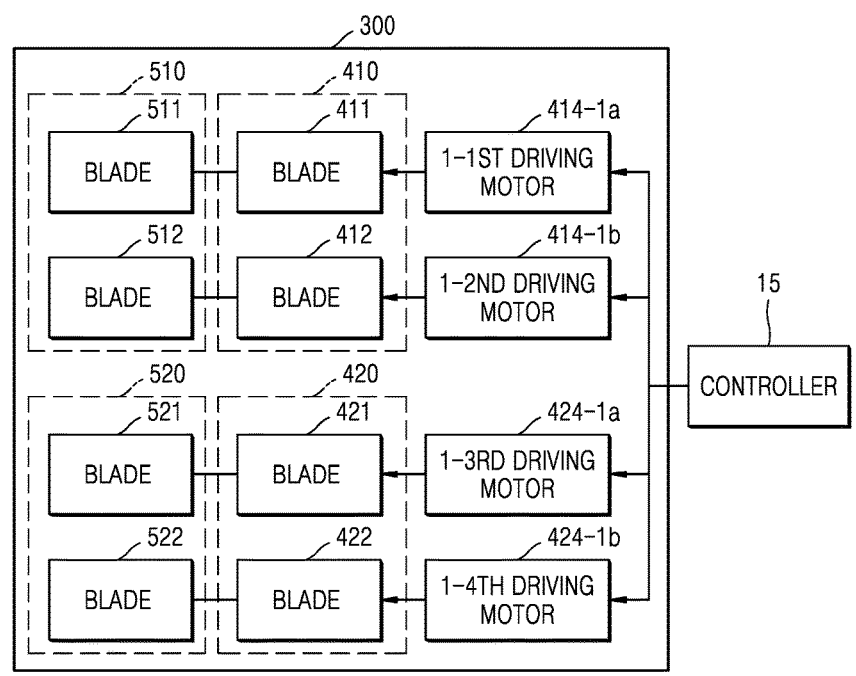
FIG. 12 is a block diagram illustrating a structure of the collimator, according to another embodiment of the present disclosure.
Figure 13:
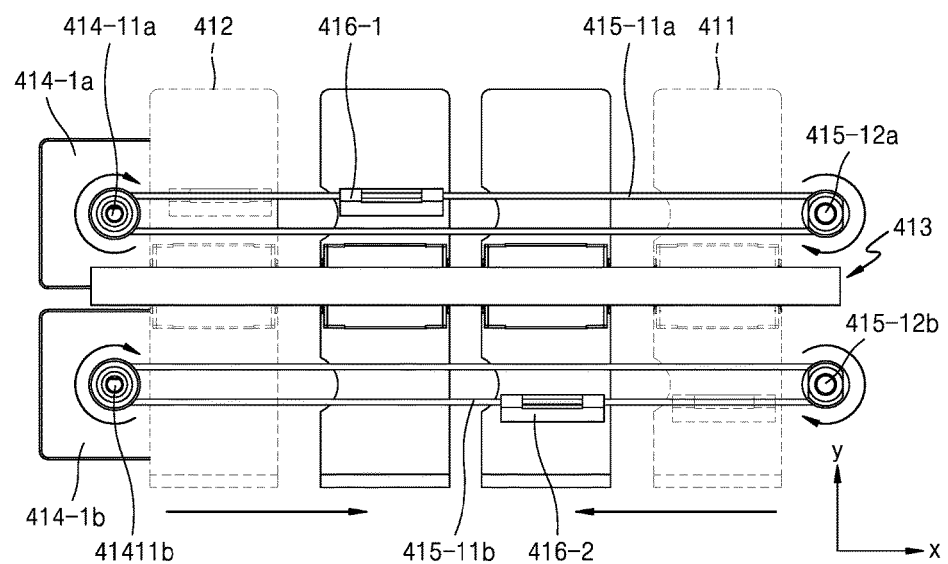
FIG. 13 is a front view illustrating the first iris unit which shows a movement status of the first and second blades of the first field range adjustor, according to another embodiment of the present disclosure.

FIG. 12 is a block diagram illustrating a structure of the collimator, according to another embodiment. FIG. 13 is a front view illustrating the first iris unit which shows a movement status of the blades 1-1 and 2-2, according to another embodiment.

Referring to FIG. 12, the 1-1st through blades 411, 412, 421 and 422 included in the first iris unit 410 and the second iris unit 420 may be independent from each other as they receive driving power generated by the 1-1st driving motor 414-1a, the 1-2nd driving motor 414-1b, the 1-3rd driving motor 424-1a, and the 1-4th driving motor 424-1b. In this case, the blades 511, 512, 521 and 522 included in a first blocking unit 510 and a second blocking unit 520 may be connected to move in synchronization with the 1-1st through blades 411, 412, 421 and 422. Hereinafter, for convenience of explanation, movements of the blade 411 and the blade 412 and the blade 511 and the blade 521 will be described, by mainly focusing on the blade 411 and the blade 412 included in the first iris unit 410 and the 2-1st blade 511 and the blade 521 included in the first blocking unit 510.

Referring to FIG. 13, as driving power is generated by the 1-1st driving motor 414-1a and the 1-2nd driving motor 414-1b, the first output axis 414-11a and the second output axis 414-11b may revolve. The first timing belt 415-11a supported to revolve by the first output axis 414-11a and the first support axis 415-12a, and the second timing belt 415-11b supported to revolve by the second output axis 414-11b and the second support axis 415-12b may revolve in the same direction as the first output axis 414-11a and the second output axis 414-11b with the first output axis 414-11a and the second output axis 414-11b rotating. In various embodiments, in the case that the first output axis 414-11a rotates clockwise, the first timing belt 415-11a may also revolve clockwise, and in the case that the second output axis 414-11b rotates counter-clockwise, the second timing belt 415-11b may also revolve counter-clockwise.

As the first timing belt 415-11a revolves clockwise and the second timing belt 415-11b revolves counter-clockwise, the first connecting member 416-1 and the second connecting member 416-2, arranged to be fixed to the first timing belt 415-11a and the second timing belt 415-1b respectively, may move in different directions along the X-axis. In this case, the first connecting member 416-1 and the second connecting member 416-2 may move independently from each other because the first connecting member 416-1 and the second connecting member 416-2 are fixed to the first timing belt 415-11a and the second timing belt 415-1b, respectively. That is, as the first timing belt 415-11a and the second timing belt 415-11b revolve in different directions, the first connecting member 416-1 and the second connecting member 416-2 may move different distances in different directions along the axis X. In some embodiments, in the case that the first timing belt 415-11a and the second timing belt 415-11b revolve in the same direction, it is obvious that the first connecting member 416-1 and the second connecting member 416-2 may move in the same direction along the axis X.

The blade 411 and the blade 412 arranged to be fixed to the first connecting member 416-1 and the second connecting member 416-2 may move independently from each other along the X-axis together with the first connecting member 416-1 and the second connecting member 416-2. As the 1st blade 411 and the blade 412 move independently from each other along the X-axis, the 1st blade 511 and the blade 512 connected to move in synchronization with the 1st blade 411 and the blade 412 may also move independently from each other. As a result, the separation distance between the 1-1st blade 411 and the blade 412 and the blade 511 and the blade 512 may be adjusted more precisely, and the first field size range P caused by the 1st blade 411 and the blade 412 along the X-axis and the second field size range T caused by the blade 511 and the blade 512 along the X-axis may be adjusted more precisely.

Figure 14:
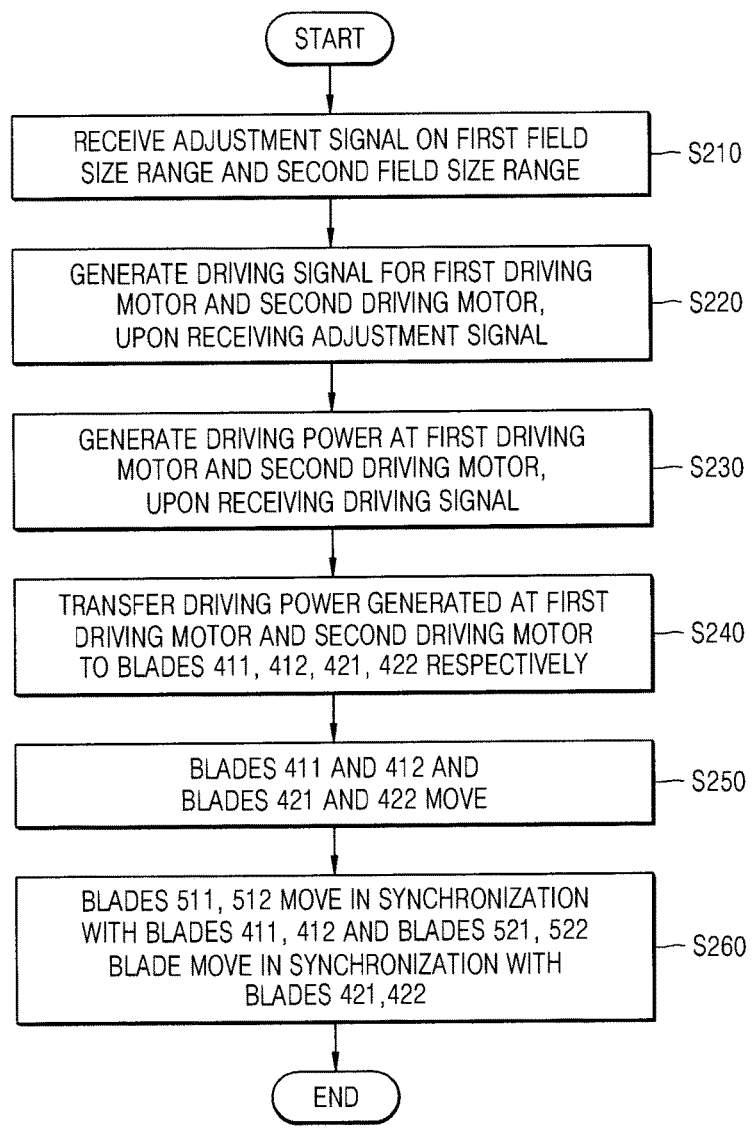
FIG. 14 is a flowchart illustrating a method of regulating the irradiation range of the X-ray imaging apparatus.

FIG. 14 is a flowchart illustrating a method of regulating the irradiation range of the X-ray imaging apparatus.

Referring to FIGS. 1, 6, 7 and 14, in operation 210, an adjustment signal on the first field size range P and the second field size range T is received. (S210)

In the X-ray imaging apparatus according to an embodiment, a user may receive the adjustment signal with respect to the first field size range P and the second field size range T formed by the collimator 300 through an input unit 142.

In operation S220, upon receiving the adjustment signal, a driving signal for the first driving motor 414-1 and the second driving motor 424-1 may be generated. (S220)

A controller 15 may generate the driving signal for the first driving motor 414-1 and the second driving motor 424-1 by using the adjustment signal received through the input unit 142 with respect to the first field size range P and the second field size range T.

In operation S230, the first driving motor 414-1 and the second driving motor 424-1 may generate driving power, upon receiving the driving signal. (S230)

The first driving motor 414-1 and the second driving motor 424-1 may generate the driving power, upon receiving the driving signal transferred from the controller 15. In this case, driving signals to drive the first driving motor 414-1 and the second driving motor 424-1 may be different from each other. As a result, driving powers generated by the first driving motor 414-1 and the second driving motor 424-1 may also be different from each other.

In operation S240, the driving power generated by the first driving motor 414-1 and the second driving motor 424-1 may be transferred to the blade 411 and the blade 412 and the blade 421 and the blade 422, respectively. (S240)

The driving power generated by the first driving motor 414-1 and the second driving motor 424-1 may be transferred to the blade 411 and the blade 412 and the blade 421 and the blade 422 through the first driving power transfer unit 415 and the second driving power transfer unit 425. In this case, the 1-1st blade 411 and the blade 412 may receive the driving power generated by the first driving motor 414-1 through the first driving power transfer unit 415, and the blade 421 and the blade 422 may receive the driving power generated by the second driving motor 424-1 through the second driving power transfer unit 425.

In operation S250, the blade 411 and the blade 412 and the blade 421 and the blade 422 may move. (S250)

The blade 411 and the blade 412 which received the driving power generated by the first driving motor 414-1 through the first driving power transfer unit 415 may move in synchronization with each other, and the blade 421 and the blade 422 which received the driving power generated by the second driving motor 424-1 through the second driving power transfer unit 425 may also move in synchronization with each other. However, as previously described in detail, as the driving power generated at the first driving motor 414-1 and the second driving motor 424-1 may be different from each other, the blade 411 and the blade 412 and the blade 421 and the blade 422 may move independently.

In operation 260, the blade 511 and the blade 512 may move in synchronization with the blade 411 and the blade 412, and the blade 521 and the blade 522 may also move in synchronization with the blade 421 and the blade 422. (S260)

As the blade 411 and the blade 412 move, the blade 511 and the blade 512 arranged to move in synchronization with the blade 411 and the blade 412 may be moved, by using the connector 600. In some embodiments, as the blade 421 and the blade 422 move, the blade 521 and the blade 522 arranged to move in synchronization with the blade 421 and the blade 422 may be moved, by using the connector 600. As a result, by driving just the first driving motor 414-1 and the second driving motor 424-1, which may drive the blade 411 and the blade 412 and the blade 421 and the blade 422, it is possible to adjust the movement range of the blade 511 and the blade 512 and the blade 521 and the blade 522, and thus, it is possible to adjust the first field size range P and the second field size range T.

Figure 15:
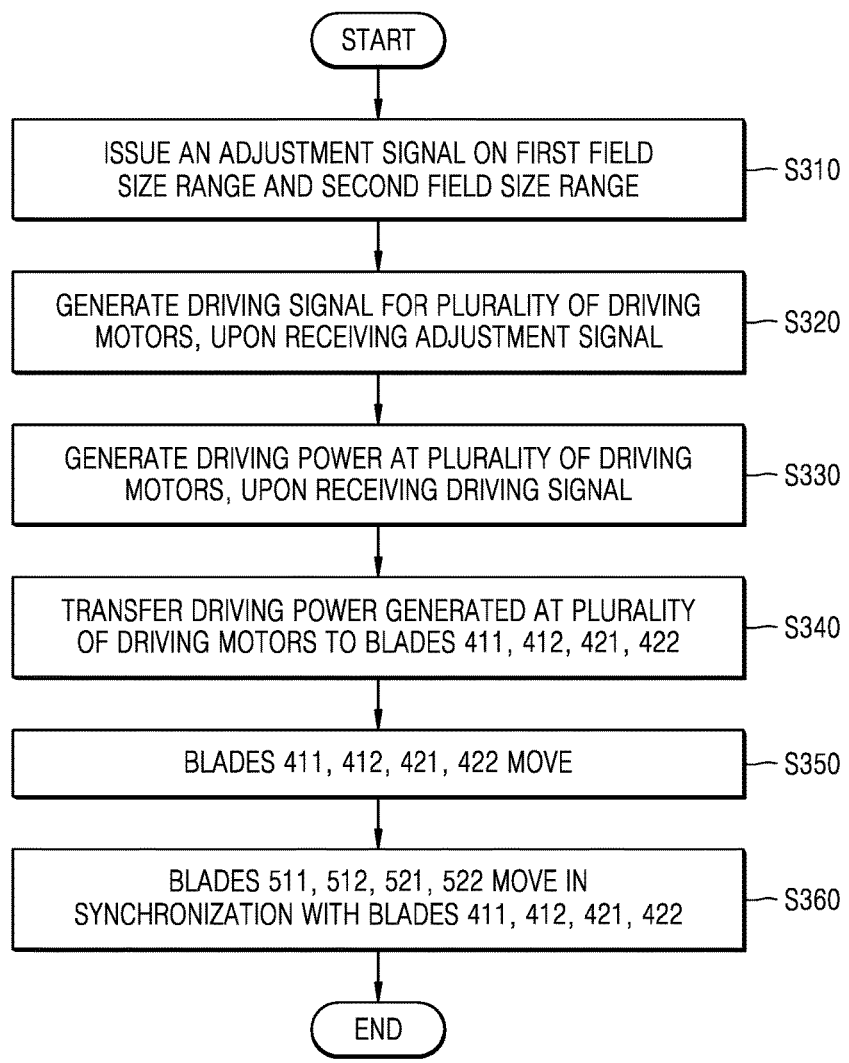
FIG. 15 is a flowchart illustrating a method of regulating the irradiation range for the X-ray imaging apparatus, according to another embodiment of the present disclosure.

FIG. 15 is a flowchart illustrating a method of regulating the irradiation range for the X-ray imaging apparatus, according to another embodiment.

Referring to FIGS. 1, 10, 11 and 13, in operation S310, an adjustment signal with respect to the first field size range P and the second field size range T is received. (S310)

In the X-ray imaging apparatus according to an embodiment, a user may receive an adjustment signal with respect to the first field size range P and the second field size range T formed by the collimator 300 through an input unit 142.

In operation S320, a driving signal for a plurality of driving motors is generated depending on the received adjustment signal. (S320)

The controller 15 may generate a driving signal for the plurality of driving motors by using an adjustment signal received with respect to the first field size range and the second field size range through the input unit 142. The plurality of driving motors are the 1-1st driving motor 414-1a, the driving motor 414-1b, the 2-1st driving motor 424-1a and the driving motor 424-1b which may drive the blades 411, 412, 421 and 422, respectively.

In operation S330, the plurality of driving motors may generate driving power, upon receiving a driving signal. (S330)

The plurality of driving motors may generate driving power, upon receiving the driving signal transferred from the controller 15. In this case, the driving signal to drive the plurality of driving motors (i.e., the 1-1st driving motor 414-1a, the driving motor 414-1b, the 2-1st driving motor 424-1a, and the driving motor 424-1b) may be different from each other. As a result, driving power generated by the 1-1st driving motor 414-1a, the driving motor 414-1b, the 2-1st driving motor 424-1a, and the driving motor 424-1b may also be different from each other.

In operation S340, driving power generated by the plurality of driving motors may be transferred to the blades 411, 412, 421 and 422, respectively. (S340)

Driving power generated by the plurality of driving motors (i.e., the 1-1st driving motor 414-1a, the driving motor 414-1b, the 2-1st driving motor 424-1a, and the driving motor 424-1b) may be transferred to the blades 411, 412, 421 and 422. In this case, the blades 411, 412, 421, and 422 may be transferred driving power generated by the plurality of driving motors through the plurality of the driving power transfer units.

In operation S350, the blades 411, 412, 421 and 422 may move. (S350)

Driving power generated by the plurality of driving motors (i.e., the 1-1st driving motor 414-1a, the driving motor 414-1b, the 2-1st driving motor 424-1a, and the driving motor 424-1b) may be different from each other. As a result the blades 411, 412, 421 and 422 may move independently from each other.

In operation S360, the blades 511, 512, 521 and 522 may move in synchronization with the blades 411, 412, 421 and 422. (S360)

As the blades 411, 412, 421 and 422 move, the 1st blade 511 and the blade 512 arranged to move in synchronization with the blades 411, 412, 421 and 422 may be moved, by using the connector 600. As a result, by driving just the plurality of driving motors (i.e., the 1-1st driving motor 414-1a, the driving motor 414-1b, the 2-1st driving motor 424-1a, and the driving motor 424-1b), which may drive the blades 411, 412, 421 and 422, it is possible to adjust the movement range of the blades 511, 512, 521 and 522, and thus, it is possible to adjust the first field size range P and the second field size range T.

The X-ray imaging apparatus according to an embodiment may prevent image defects, which may be caused by such problems as a control error, by using a plurality of X-ray field size range adjustment units which are arranged to move in synchronization with each other.

In addition, it is possible to improve manufacturing convenience and reduce manufacturing costs, as the plurality of X-ray field size range adjustment units may be adjusted by using one driving motor.

Although the X-ray imaging apparatus and the method of operating the X-ray imaging apparatus according to one or more embodiments have been described with reference to the figures, the aforementioned embodiments are merely examples. It will be understood by those of ordinary skill in the art that various changes in form and details may be made therein without departing from the spirit and scope of the present invention as defined by the following claims.

What is claimed is:
1. An X-ray imaging apparatus comprising:
an X-ray source configured to irradiate an X-ray; and a collimator configured to adjust an irradiation range of the X-ray irradiated from the X-ray source, wherein the collimator comprises:
  a first field size range adjustor comprising a first plurality of blades and a driving power transfer unit configured to transfer driving power to the first plurality of blades;
  a second field size range adjustor facing the first field size range adjustor and comprising a first plurality of blades; and
  a connector configured to respectively connect the first plurality of blades of the first field size range adjustor to the first plurality of blades of the second field size range adjustor so as to make the first plurality of blades of the second field size range adjustor move as the first plurality of blades of the first field size range adjustor move,
wherein:
  the driving power transfer unit comprises a timing belt,
  the timing belt comprises a plurality of timing belts,
  the plurality of timing belts comprises a first timing belt and a second timing belt,
  the first plurality of blades of the first field size range adjustor comprises a first blade, a second blade, a third blade, and a fourth blade,
  the first blade and the second blade of the first plurality of blades of the first field size range adjustor face each other and are coupled to the first timing belt, and
  the third blade and the fourth blade of the first plurality of blades of the first field size range adjustor face each other and are coupled to the second timing belt.

2. The X-ray imaging apparatus of claim 1, further comprising:
  a plurality of driving motors configured to transfer driving power to the timing belts and comprising a first driving motor and a second driving motor,
  wherein
  the first driving motor is configured to transfer driving power to the first timing belt and the second driving motor is configured to transfer driving power to the second timing belt.

3. The X-ray imaging apparatus of claim 2, further comprising:
  a controller configured to transfer a driving signal to the first driving motor and the second driving motor,
  wherein the controller transfers control signals respectively to the first driving motor and the second driving motor such that the first blade and the second blade of the first plurality of blades of the first field size range adjustor are movable independently from the third blade and the fourth blade of the first plurality of blades of the first field size range adjustor.

4. The X-ray imaging apparatus of claim 1, further comprising:
  a first slide support unit configured to allow the first blade and the second blade of the first plurality of blades of the first field size range adjustor to slidably move, wherein the first blade and the second blade of the first plurality of blades of the first field size range adjustor are movable along the first slide support unit; and
  a second slide support unit configured to allow the third blade and the fourth blade of the first plurality of blades of the first field size range adjustor to slidably move, wherein the third blade and the fourth blade of the first plurality of blades of the first field size range adjustor are movable along the second slide support unit.

5. An X-ray imaging apparatus comprising:
an X-ray source configured to irradiate an X-ray; and
a collimator configured to adjust an irradiation range of the X-ray irradiated from the X-ray source, wherein the collimator comprises:
  a first field size range adjustor comprising a first plurality of blades and a driving power transfer unit configured to transfer driving power to the first plurality of blades;
  a second field size range adjustor facing the first field size range adjustor and comprising a first plurality of blades; and
  a connector configured to provide a connection between one of the first plurality of blades of the first field size range adjustor and one of the first plurality of blades of the second field size range adjustor so as to make s-the one of the first plurality of blades of the second field size range adjustor move as the one of the first plurality of blades of the first field size range adjustor moves,
wherein the driving power transfer unit comprises four driving power transmission belts,
wherein the first plurality of blades of the first field size range adjustor comprises a first blade and a second blade which face each other and a third blade and a fourth blade which face each other, and
wherein the first blade, the second blade, the third blade, and the fourth blade are coupled to the four driving power transmission belts respectively.

6. The X-ray imaging apparatus of claim 5, further comprising:
  a plurality of driving motors configured to transfer driving power to the four driving power transmission belts.

7. The X-ray imaging apparatus of claim 6, further comprising:
  a controller configured to transfer control signals respectively to corresponding ones of the plurality of driving motors causing the first blade, the second blade, the third blade, and the fourth blade of the first plurality of blades of the first field size range adjustor to move independently from each other.

8. The X-ray imaging apparatus of claim 5, further comprising:
  a first slide support unit configured to allow the first blade and the second blade of the first plurality of blades of the first field size range adjustor to slidably move, wherein the first blade and the second blade of the first plurality of blades of the first field size range adjustor move along the first slide support unit; and
  a second slide support unit configured to allow the third blade and the fourth blade of the first plurality of blades of the first field size range adjustor to slidably move, wherein the third blade and the fourth blade of the first plurality of blades of the first field size range adjustor move along the second slide support unit.

9. An X-ray imaging apparatus comprising:
an X-ray source configured to irradiate an X-ray; and
a collimator configured to adjust an irradiation range of the X-ray irradiated from the X-ray source, wherein the collimator comprises:
a first field size range adjustor comprising a first plurality of blades and a driving power transfer unit configured to transfer driving power to the first plurality of blades;
a second field size range adjustor facing the first field size range adjustor and comprising a first plurality of blades; and a connector configured to provide a connection between one of the first plurality of blades of the first field size range adjustor and one of the first plurality of blades of the second field size range adjustor so as to make the one of the first plurality of blades of the second field size range adjustor move as the one of the first plurality of blades of the first field size range adjustor moves, wherein the connector comprises a connecting link arranged to revolve around a hinge unit, and a linking unit configured to connect the one of the first plurality of blades of the first field size range adjustor and the one of the first plurality of blades of the second field size range adjustor by using the connecting link.

10. The X-ray imaging apparatus of claim 9, wherein the linking unit further comprises:

a first long hole formed along a lengthwise direction of the connecting link in the connecting link;

a first slider coupled to the one of the first plurality of blades of the first field size range adjustor and to be movable in the first long hole;

a second long hole formed along the lengthwise direction of the connecting link in the connecting link; and a second slider coupled to the one of the first plurality of blades of the second field size range adjustor and to be movable in the second long hole.

11. The X-ray imaging apparatus of claim 10, wherein a movement ratio of the one of the first plurality of blades of the first field size range adjustor to the one of the first plurality of blades of the second field size range adjustor which is connected to the one of the first plurality of blades of the first field size range adjustor is the same as a distance ratio of a distance from the hinge unit to the first slider to a distance from the hinge unit to the second slider.

12. A method of operating an X-ray imaging apparatus comprising an X-ray source configured to irradiate an X-ray and a collimator comprising a first field size range adjustor and a second field size range adjustor, the method comprising:

detecting a first adjustment signal corresponding to a first field size range and a second adjustment signal corresponding to a second field size range;

moving a first plurality of blades of the first field size range adjustor; and moving a first plurality of blades of the second field size range adjustor in synchronization with the first plurality of blades of the first field size range adjustor, wherein a driving power transfer unit of the first field size range adjustor comprises four driving power transmission belts, wherein the first plurality of blades of the first field size range adjustor comprises a first blade and a second blade which face each other and a third blade and a fourth blade which face each other, and wherein the first blade, the second blade, the third blade, and the fourth blade are coupled to the four driving power transmission belts respectively.

13. The method of claim 12, wherein the first plurality of blades of the second field size range adjustor comprise a first blade, a second blade, a third blade, and a fourth blade, and wherein the method further comprises:

generating a driving signal for a first driving motor and a second driving motor upon receiving the first adjustment signal and the second adjustment signal;

generating driving power by the first driving motor and the second driving motor upon receiving the driving signal; and transferring the driving power generated by the first driving motor to the first and second blades of the first plurality of blades for the first field size range adjustor and the driving power generated by the second driving motor to the third and fourth blades of the first field size range adjustor, respectively.

14. The method of claim 13, further comprising:

providing independent driving signals to the first driving motor and the second driving motor; and moving the first and second blades of the first plurality of blades for the first field size range adjustor independently from the third and fourth blades of the first plurality of blades of the first field size range adjustor upon receiving the driving signals.

15. The method of claim 12, wherein the first plurality of blades of the second field size range adjustor comprise a first blade, a second blade, a third blade, and a fourth blade; and wherein the method further comprises:

generating a driving signal for a plurality of driving motors upon receiving the first adjustment signal and the second adjustment signal;

generating driving power at the plurality of driving motors upon receiving the driving signal; and transferring the driving power generated at the plurality of driving motors to each of the first blade, second blade, third blade, and fourth blade of the first plurality of blades of the first field size range adjustor, respectively.

16. The method of claim 15, wherein independent driving signals are respectively provided to the plurality of driving motors; and the first blade, the second blade, the third blade, and the fourth blade of the first plurality of blades of the first field size range adjustor are moved independently from each other.

* * * * *

UNITED STATES PATENT AND TRADEMARK OFFICE
CERTIFICATE OF CORRECTION

PATENT NO.         : 10,241,060 B2
APPLICATION NO.    : 15/156615
DATED              : March 26, 2019
INVENTOR(S)        : Dae-soo Kim Page 1 of 1

It is certified that error appears in the above-identified patent and that said Letters Patent is hereby corrected as shown below:

In the Claims

Column 24, Claim 5, Line 17 should read as follows:
--…to make the one of…--

Signed and Sealed this
Thirtieth Day of April, 2019

Andrei Iancu
*Director of the United States Patent and Trademark Office*